United States Patent [19]
Moss et al.

[11] Patent Number: 5,834,310
[45] Date of Patent: Nov. 10, 1998

[54] MAMMALIAN MUSCLE NAD: ARGININE ADP-RIBOSYLTRANSFERASE

[75] Inventors: Joel Moss, Bethesda; Ian Okazaki; Anna Zolkiewska, both of Rockville; Maria S. Nightingale, Bethesda, all of Md.

[73] Assignee: The United States of America as represented by the Department of Health and Human Services, Washington, D.C.

[21] Appl. No.: 896,410

[22] Filed: Jul. 18, 1997

Related U.S. Application Data

[60] Continuation of Ser. No. 454,556, May 30, 1995, abandoned, which is a division of Ser. No. 985,698, Nov. 30, 1992, abandoned.

[51] Int. Cl.$^6$ .............................. C12N 1/20; C07H 21/04
[52] U.S. Cl. ................. 435/325; 435/252.3; 435/252.33; 435/320.1; 435/350; 435/351; 435/352; 435/353; 435/354; 435/193; 435/194; 536/23.2; 536/23.1; 536/23.5
[58] Field of Search ..................... 435/193, 194, 435/325, 252.3, 252.33, 320.1, 350, 351–354; 536/23.2, 23.1, 23.5

[56] References Cited

U.S. PATENT DOCUMENTS

| | | | |
|---|---|---|---|
| 4,289,690 | 9/1981 | Pestka et al. | 260/112 R |
| 4,399,216 | 8/1983 | Axel et al. | 435/6 |
| 4,634,665 | 1/1987 | Axel et al. | 435/68 |
| 4,675,285 | 6/1987 | Clarke et al. | 435/6 |
| 4,683,195 | 7/1987 | Mullis et al. | 435/6 |
| 4,792,520 | 12/1988 | Stambrook et al. | 435/6 |
| 4,948,882 | 8/1990 | Ruth | 536/29 |

FOREIGN PATENT DOCUMENTS 2244704  12/1991  United Kingdom .

OTHER PUBLICATIONS

Abersold, et al. *Proc. Natl. Acad. Sci 84:* 6970–6974 (1987).
Allured, et al. *Proc. Natl. Acad. Sci* 83: 1320–1324 (1986).
Brune, et al. *Proc. Natl. Acad.Sci* 87: 3304–3308 (1990).
Chomczynski, et al. *Anal. Biochemistry* 162: 156–159 (1987).
Davis, et al. *Basic Methods in Molecular Biology* pp. 348–354, Elsevier Press, NY (1986).
Fendrick, et al. *Eur. J. Biochem.* 205: 25–31 (1992).
Frohman, et al. *Technique: A Journal of Methods in Cell and Molecular Biology* 1(3):165–170 (1989).
Frohman, et al. *Proc. Natl. Acad. Sci* 85: 8998–9002 (1988).
Kharadia, et al. *Exp. Cell Research* 201: 33–42 (1992).
Larew, et al. *J. of Biol. Chem.* 266(1) : 52–57 (1991).
Moss, et al. *Proc. Natl. Acad. Sci* 82: 5603–5607 (1985).
Moss, et al. *J. of Biol. Chem.* 255(12) : 5838–5840 (1980).
Moss, et al. *J. of Biol. Chem.* 267(15) : 10481–10488 (1992).
Moss, et al. *Adv. Enzymol.* 61: 303–379 (1988).
Nicosia, et al. *Proc. Natl. Acad. Sci* 83: 4631–4635 (1986).
Obara, et al. *Eur. J. Biochem.* 200: 75–80 (1991).
Peterson, et al. *J. of Biol. Chem.* 265(28) : 17062–17069 (1990).
Rabilloud, et al. *Electrophoresis* 9: 288–291 (1988).
Sixma, et al. *Nature* 351: 371–377 (1991).
Soman, et al. *Biochem. and Biophys. Commun.* 120(3): 973–980 (1984).
Soman, et al. *Biochem. and Biophys. Commun.* 176:301–308 (1991).
Taniguchi, et al. *Biochem. and Biophys. Commun.* 164(1): 128–133 (1989).
Tanuma, et al. *FEBS* 261(2) : 381–384 (1990).
Tanuma, et al. *J. of Biol. Chem.* 263(11) : 5485–5489 (1988).
Udenfriend, et al. *Cell. and Mol. Biol.* 38(1) : 11–16 (1992).
Ueda, et al. *Ann. Rev. Biochem.* 54: 73–100 (1985).
West, et al. *Biochemistry* 25: 8057–8062 (1986).
Yost, et al. *J. of Biol. Chem.* 258(8) : 4926–4929 (1983).
Aktories, et al. *Biochemical & Biophysical Res. Commun.* 158(1) : 209–213 (1989).
Barbieri, et al. *Infection and Immunity* 56(8):1934–1941 (1988).
Beckner, et al. *FEBS Letters* 95(2) : 319–322 (1978).
Bhatia, et al. *J. of Cell. Physiology* 144: 345–353 (1990).
Farzaneh, et al. In: *ADP–ribose Transfer Reactions: Mechanisms and Biological Significance.* Springer–Verlag, New York pp. 189–193 (1989).
Farzaneh, et al. *Nucleic Acids Res.* 16(23):11319–11326 (1988).
Fitzmaurice, et al. *Mol. Gen. Genet.* 218: 340–347 (1989).
Fu, et al. *Proc. Natl. Acad. Sci.* 87: 1720–1724 (1990).
Herzog, et al. *Proc. Natl. Acad. Sci.* 86: 3514–3518 (1989).
Ikejima, et al. *Biochemical & Biophysical Res. Commun.* 163(2) : 739–745 (1989).
Kalsow, et al. *J. of Biological Chem.* 264(11) : 6386–6390 (1989).
Kuppert, et al. *J. of Biological Chem.* 265(31):18721–18724 (1990).
Nemoto, et al. *J. of Biological Chem.* 266(29):19312–19319 (1991).
Ogorochi, et al. *Biochemical & Biophysical Res. Commun.* 163(2):1175–1181 (1989).
Pero, et al. *Carcinogenesis* 6(7):1055–1058 (1985).
Peterson, et al. *J. of Biological Chem.* 365(28):17062–17069 (1990).
Pizza, et al. *Proc. Natl. Acad. Sci.* 85: 7521–7525 (1988).
Popoff, et al. *Nucleic Acids Res.* 18(5) : 1291 (1990).
Price, et al. *Proc. Natl. Acad. Sci.* 85: 5488–5491 (1988).

(List continued on next page.)

*Primary Examiner*—Robert A. Wax
*Assistant Examiner*—Nashaat T. Nashed
*Attorney, Agent, or Firm*—Knobbe, Martens, Olson & Bear, LLP

[57] ABSTRACT

This invention relates to the identification and molecular characterization of NAD:arginine ADP-ribosyltransferases. Sequences from the rabbit skeletal muscle NAD:arginine ADP-ribosyltransferase and the human NAD:arginine ADP-ribosyltransferase are provided herein. Recombinant protein is expressed from a recombinant gene vector containing at least 15 continuous bases of genes encoding these sequences.

6 Claims, 1 Drawing Sheet

OTHER PUBLICATIONS

Schneider, et al. *Eur. J. of Cell Biol.* 44: 302–307 (1987).

Strain, A. *Exp Cell Res.* 159:531–535 (1985).

Taniguchi, et al. *Eur. J. Biochem.* 195: 557–562 (1991).

Taniguchi, et al. *Eur. J. Biochem.* 171: 571–575 (1988).

Troll, et al. *Basic Life Science* 52: 225–232 (1990).

Tsuchiya, et al. *J. of Biological Chem.* 266(5) : 2772–2777 (1991).

Zolkiewska, et al. *Molecular Characterization of NAD: Arginine ADP–Ribosyltransferase From Rabbit Skeletal Muscle Proc. Natl. Acad. Sci.* 89: 11352–11356 (1992).

Welsh, et al. *Fed. Am. Soc. Exp. Biol.* (FASEB) 5(4) : A821 (1991).

Wozniak, et al. *Proc. Natl. Acad. Sci.* 85: 8880–8884 (1988).

Watson, et al. *Molecular Biology of the Gene 4th Ed. Benjamin/Cummings Publ. Co., Menlo Park, CA* p. 313 (1988).

Maniatis, et al. *Molecular Cloning A Laboratory Manual, Second Ed., Cold Spring Harbor Laboratory Press, Cold Spring Harbor, NY* pp. xx, xxi, xxiv, xxv, xxvi, xxix, xxx, xxxi, xxxiv, xxxv, 11.2–11.19 and 14.2–14.35 (1989).

MAMMALIAN MUSCLE NAD: ARGININE ADP-RIBOSYLTRANSFERASE

This application is a continuation of U.S. patent application Ser. No. 08/454,556, filed May 30, 1995, (now abandoned) which is a divisional of U.S. patent application Ser. No. 07/985,698, filed Nov. 30, 1992 (now abandoned).

RELATED APPLICATIONS

The present application is a divisional application of International Application No. PCT/US93/11569 which in its United States designation is a continuation-in-part of U.S. application Ser. No. 07/985,698, filed Nov. 30, 1992. The complete disclosures of these related applications are hereby incorporated herein by this reference thereto.

FIELD OF THE INVENTION

This invention relates to vertebrate ADP-ribosyltransferases and specifically to mono-ADP-ribosyltransferases. In particular this invention relates to the purification, isolation and identification of mono-NAD:arginine ADP-ribosyltransferases.

BACKGROUND OF THE INVENTION

Mono-ADP-ribosylation is a post-translational event resulting in the covalent modification of proteins. ADP-ribosyltransferases and ADP-ribosylarginine hydrolases are responsible for the forward and reverse reactions that control the ADP-ribosylation of cellular proteins. In some systems, i.e. bacterial toxin ADP-ribosyltransferases, the extent of protein ADP-ribosylation is a critical determinant of enzymatic activity.

Mono-ADP-ribosylation is involved in the action of bacterial toxins and in the regulation of cellular processes in prokaryotes and eukaryotes (Moss, et al. *Adv. Enzymol.* 61: 303–379 (1988); Lowery, et al. and Williamson, et al. *ADP-ribosylating Toxins and G Proteins: Insights into Signal Transduction*, (1990) eds. Moss, J. et al. pp. 459–477 and pp. 493–510). Cholera toxin is a secretory product of the microorganism Vibrio cholera. This toxin is responsible for the pathogenesis of cholera. The cholera toxin directs the ADP-ribosylation of guanine nucleotide-binding proteins which in turn enhances their activity and increases the responsiveness of some animal cells to various hormones, neurotransmitters and drugs (Moss, et al. supra and Ueda, K., et al. *Ann. Rev. Biochem.* 54:73–100, 1985).

Several ADP-ribosylating toxins have been cloned from bacteria (Nicosia, et al. *Proc. Natl. Acad. Sci. (USA)* 83: 4631–4635, 1986 and Nemoto, et al. *J. Biol. Chem.* 266: 19312–19319, 1991) and the crystal structures of some of the toxins have been solved (Allured, et al. *Proc. Natl. Acad. Sci. (USA)* 83: 1320–1324, 1986 and Sixma, et al. *Nature* 351: 371–377, 1991). While the bacterial toxins have similarities to one another in their amino acid sequences, the enzymes differ in the amino acids that they modify. Arginine, cysteine, asparagine and diphthamide (modified histidine) serve as ADP-ribose acceptors for Cholera toxin, pertussis toxin, botulinum C3 transferase and diphtheria toxin respectively.

Within prokaryotic and eukaryotic cells, ADP-ribosylation appears to be a reversible modification of proteins. An ADP-ribosylation cycle is involved in the regulation of the nitrogenase of the photosynthetic bacterium *Rhodospirillium rubrum* (Lowery, et al. supra). Here, an ADP-ribosyltransferase is responsible for the inactivation of the nitrogenase, whereas an ADP-ribosylarginine hydrolase releases the ADP-ribose moiety and activates the nitrogenase.

The role of mono-ADP-ribosylation in eukaryotes is less well-characterized; however, it is postulated that families of mono-ADP-ribosyltransferases will be identified in a given species and that these mono-ADP-ribosyltransferases will share homologies within their gene sequences. Eukaryotic mono-ADP-ribosyltransferases are believed to be involved in a number of physiological processes such as the regulation of adenylyl cyclase (Obara, et al. *Eur. J. Biochem.* 200: 75–80, 1991; Brune, et al. *Proc. Natl. Acad. Sci. USA* 87: 3304–3308, 1990; Fendrick, et al. *Eur. J. Biochem.* 205: 25–31 (1992); and Kharadia, et al. *Exp. Cell. Res.* 201: 33–42, 1992). While it is believed that there are families of mono-ADP-ribosyltransferases located in different tissues, the gene sequences of this invention will be useful for verifying this hypothesis. Arginine- and cysteine-specific ADP-ribosyltransferases and ADP-ribosylarginine and ADP-ribosylcysteine hydrolases have been identified in animal tissues, consistent with the presence of ADP-ribosylation cycles responsible for the reversible ADP-ribosylation of arginine and cysteine residues in proteins (Moss, et al. *Proc. Natl. Acad. Sci. USA* 82: 5603–5607, 1985; Tanuma, et al. *J. Biol. Chem.* 263: 5485–5489, 1988; and Tanuma, et al. *FEBS Lett.* 261: 381–384, 1990).

ADP-ribosylarginine hydrolase has been purified from turkey erythrocytes and rat brain. Further, the ADP-ribosylarginine hydrolase has been cloned from rat brain (Moss, et al. *J. Biol. Chem.* 267: 10481–10488, 1992). NAD:Arginine ADP-ribosyltransferases have been purified from turkey erythrocytes (Moss, et al. *J. Biol. Chem.* 255: 5838–5840, 1980; Yost, et al. *J. Biol. Chem.* 258: 4926–4929, 1983) and rabbit skeletal muscle (Taniguchi, et al. *Biochem. Biophys. Res. Commun.* 164: 128–133, 1989 and Peterson, et al. *J. Biol. Chem.* 265: 17062–17069, 1990). However, the gene sequences for these enzymes have remained unidentified until now. In turkey erythrocytes there is a family of ADP-ribosyltransferase enzymes that differ in their localization within the cell as well as in their physical, regulatory and kinetic properties (Williamson, et al., Moss, et al. *J. Biol. Chem.*, Yost, et at, all supra, and West, et al. *Biochemistry* 25: 8057–8062, 1986). The turkey ADP-ribosyltransferases appear to be ubiquitous in their tissue distribution, while the rabbit ADP-ribosyltransferase is located primarily within the sarcoplasmic reticulum of cardiac and skeletal muscle. Neither the RNA nor the DNA sequence of any mono-ADP-ribosyltransferases have been previously identified from a eukaryotic system There are significant differences between the bacterial ADP-ribosyltransferases and eukaryotic ribosyltransferases. For example, since the bacterial toxins differ from the animal transferases in substrate specificity, therapies directed toward ADP-ribosyltransferases cannot rely on cloned bacterial enzymes. Eukaryotic ADP-ribosyltransferases are required for this work. In addition, the bacterial enzymes differ from their mammalian counterpart in their sensitivity to inhibitors. Therefore, it would be more valuable to test the effect of different inhibitors on eukaryotic enzymes than on their bacterial counterparts. Finally, bacterial transferases are targeted by a system different from those used with the animal transferases and therefore, the recombinant bacterial enzymes may localize to different compartments within animal cells. The bacterial toxins function by binding to the outside of a eukaryotic cell and delivering their catalytic subunit to the cells. The eukaryotic enzymes are intracellular enzymes that are required for effective protein regulation.

Few ADP-ribosyltransferases have been purified from animal cells. Moss, et al. purified an ADP-ribosyltransferase from turkey erythrocytes. In another example, Peterson, et al. (supra), purified an enzyme from the same organ system and species used in the instant invention. This enzyme had an activity in vitro that was predictive of a mono-ADP-ribosyltransferase; however, the protein was not purified to a level that would permit someone to obtain useful tryptic digest information. Prediction of the gene sequence requires tryptic digest information. While the protein of Peterson, et al. can be used to study the enzymatic properties of a mono-ADP-ribosyltransferase, gene therapeutic strategies cannot be pursued nor can studies be conducted to assess the effect of the ADP-ribosyltransferase, or a mutated ADP-ribosyltransferase, on cell metabolism. Modification of cellular metabolism requires an ADP-ribosyltransferase gene, as produced in the present invention. Similarly, to develop a therapeutic modality in humans, a human enzyme is particularly preferred primarily for immunological reasons.

Once a vertebrate ADP-ribosyltransferase is identified, the gene can be used to isolate other ADP-ribosyltransferases, including the human counterpart. The human sequence is heretofore undefined. Therefore, it is an object of the present invention to identify the gene sequence for vertebrate mono-ADP-ribosyltransferases in general and for human mono-ADP-ribosyltransferase in particular.

SUMMARY OF THE INVENTION

This invention provides the amino acid and nucleotide sequence of a rabbit and human mono-ADP-ribosyltransferase. Oligonucleotide fragments from these sequences are useful for the further identification and isolation of homologous mono-ADP-ribosyltransferases isolated from other vertebrates. Nucleotide and peptide fragments derived from these sequences are useful for the development of assays to detect the presence of the enzyme in a tissue or fluid sample from a vertebrate.

In one embodiment of the present invention, Applicants disclose an assay method for identifying a mono-ADP-ribosyltransferase gene sequence from a vertebrate comprising (a) harvesting tissue containing ADP-ribosyltransferase activity from a vertebrate, (b) purifying the mono-ADP-ribosyltransferase from the tissue, (c) obtaining fragments of the mono-ADP-ribosyltransferase, (d) sequencing peptides obtained from the fragments, (e) preparing degenerate oligonucleotides corresponding to the amino acid sequence of the peptides, (f) using the oligonucleotides in at least one polymerase chain reaction to generate nucleic acid sequences, wherein the resulting fragments correspond to at least a portion of the mono-ADP-ribosyltransferase sequence, (g) generating the nucleic acid sequence of the polymerase chain reaction fragments, (h) identifying different oligonucleotides corresponding to the mono-ADP-ribosyltransferase sequence, and (i) repeating steps (f) through (h) until the complete nucleic acid sequence is identified.

In another embodiment of the present invention an assay method is disclosed for identifying a mono-ADP-ribosyltransferase gene sequence in a vertebrate comprising (a) identifying tissue from the vertebrate that contains ADP-ribosyltransferase activity, (b) isolating mRNA from the tissue, (c) preparing cDNA from the mRNA, (d) preparing an oligonucleotide pair suitable for use in a polymerase chain reaction, one oligonucleotide of the pair having a sequence substantially the same as a first portion of SEQ ID NO:1, and the other oligonucleotide of the pair having a sequence substantially complementary to a second portion of SEQ ID NO: 1, (e) performing the polymerase chain reaction on the cDNA using the oligonucleotide pair of step (d) to generate PCR-amplified fragments, (f) sequencing the fragments generated from the polymerase chain reaction, and (g) repeating steps (e) through (g) until the cDNA is completely sequenced.

In another preferred embodiment of the present invention, an isolated or purified nucleic acid fragment encoding rabbit skeletal muscle ADP-ribosyltransferase is provided that corresponds to SEQ ID NO:1. Alternatively, the gene sequence is provided wherein the sequence is mutated in vitro to contain at least one nucleotide change in the sequence. Purified or isolated oligonucleotide is also provided that comprises at least 15 continuous bases of SEQ ID NO:1. In addition recombinant gene vectors are provided that contain at least a 15 base portion of SEQ ID NO:1 as well as recombinant protein expressed from the recombinant gene vector. Preferably, this protein is essentially pure and the protein exhibits ADP-ribosyltransferase activity. The recombinant protein is preferably expressed in eukaryotes or prokaryotes. In another preferred embodiment, gene sequences are disclosed that have at least an 85% homology to SEQ ID NO:1.

In another preferred embodiment a gene sequence is provided that encodes human ADP-ribosyltransferase, consisting essentially of the sequence corresponding to SEQ ID NO:37. In addition, recombinant gene vectors are provided that contain at least 15 continuous bases of SEQ ID NO:37. Recombinant protein expressed from the recombinant gene vector are disclosed. Preferably, the recombinant protein is essentially pure. More preferably, the recombinant protein exhibits ADP-ribosyltransferase activity. The recombinant protein is expressed in eukaryotes or prokaryotes.

In yet another preferred embodiment purified antibody is provided that is capable of specifically binding to the recombinant protein encoded by SEQ ID NO:1. In another embodiment, purified antibody is provided that is capable of specifically binding to the recombinant protein encoded by SEQ ID NO:37.

In another aspect of the present invention, there is provided an assay method for detecting an ADP-ribosyltransferase gene sequence homologous to SEQ ID NO:37 in a vertebrate comprising (a) obtaining at least one oligonucleotide pair from SEQ ID NO:37 suitable for a polymerase chain reaction and a third oligonucleotide pair selected from SEQ ID NO:3 positioned between the oligonucleotide pair, (b) isolating a tissue sample from a vertebrate, (c) processing the tissue to obtain nucleic acid suitable as a template for use in a polymerase chain reaction, (d) performing a polymerase chain reaction using the oligonucleotide pair to generate at least one DNA fragment, (e) hybridizing the third oligonucleotide with the DNA fragment and (f) detecting hybridization between the third oligonucleotide and the DNA fragment.

DETAILED DESCRIPTION OF THE INVENTION

Figure 1:
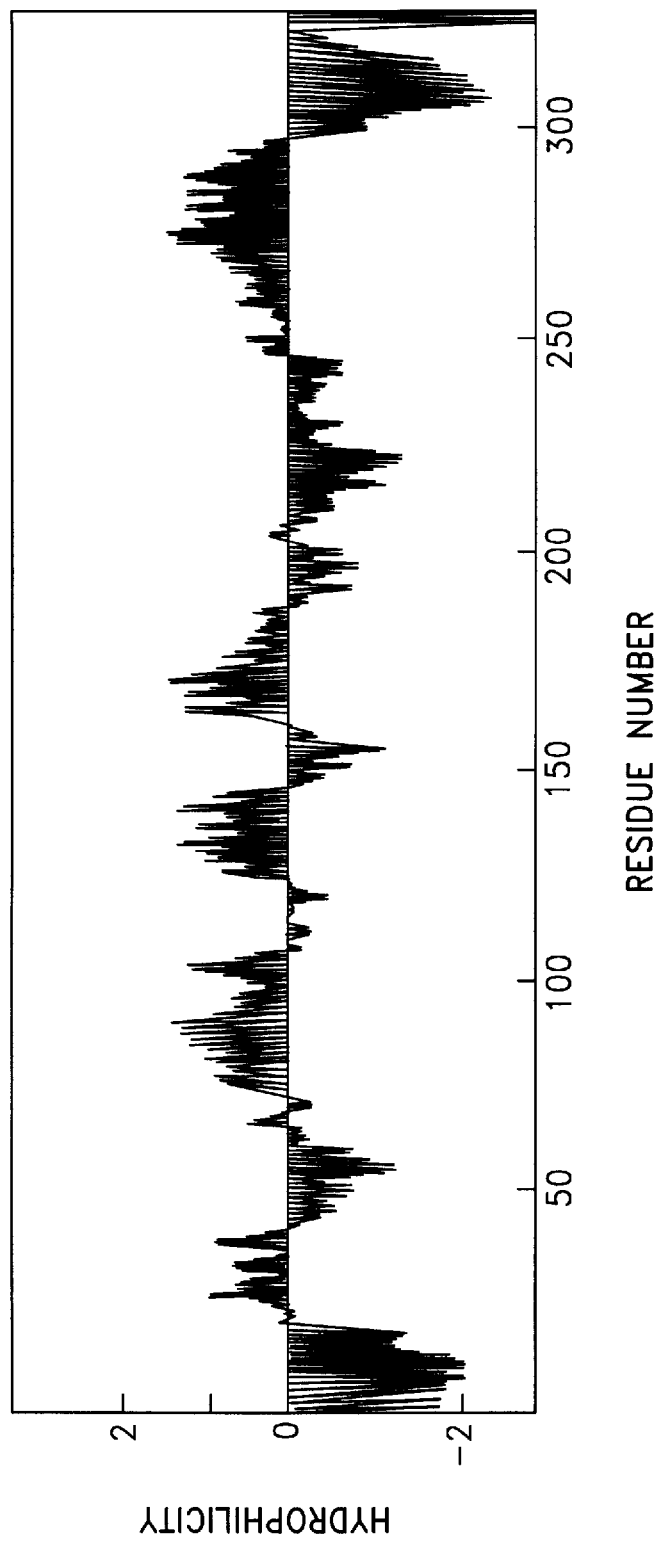
FIG. 1 is a hydrophilicity plot of the predicted amino acid sequence of the rabbit ADP-ribosyltransferase.

The gene sequence for rabbit and human muscle NAD: Arginine ADP-ribosyltransferase is disclosed. In addition, methods are disclosed for isolating and identifying sequences corresponding to NAD: Arginine ADP-ribosyltransferase from other vertebrates.

Knowledge of the gene sequence is required in order to study the effects of the enzyme on cells both in vivo and in vitro. Recombinant NAD: Arginine ADP-ribosyltransferase nucleic acid can be introduced into cells to alter the level of protein ADP-ribosylation and to modify intracellular protein activity in general. The ADP-ribosyltransferase gene, when overexpressed, can also be used to study the effect of pharmacological agents on endogenous ADP-ribosylation. Further, the identification of the gene sequence and the expression of this sequence in appropriate eukaryotic or prokaryotic cells permits the isolation of this protein in amounts suitable for purification for antibody production, the development of diagnostic reagents, and sensitive tests to detect the activity of this enzyme in cell lysates. Nucleic acid fragments of this sequence are useful as genetic probes for assessing differences in ADP-ribosyltransferase expression within a population and for the identification of ADP-ribosyltransferase mutants. The isolation of purified recombinant protein facilitates production of tests to identify inhibitors and activators of the ADP-ribosyltransferase. These agents would likely have therapeutic value in the medical community.

To identify the gene sequence, the enzyme is first purified from mammalian muscle. In Example 1, the source of enzyme was rabbit skeletal muscle. It is contemplated that the procedures disclosed herein are suitable for a variety of muscle tissue from a variety of vertebrates. While Example 1 provides a specific exemplary method, there are also a number of methods recognized in the art to purify active enzyme from tissue homogenates. The purification scheme selected should yield suitable quantities of enzyme (at least 100 picomoles) at a suitable level of purity (at least 80% pure).

The initial purification steps used in this invention (through concanavalin A agarose) were those described by Peterson, et al. (supra), with several important modifications (Table 1 and Example 1). The specific activity of the transferase identified by Peterson, et al., used two chromatographic steps (DE52 cellulose and concanavalin A agarose) to generate enzymatic activity ranging from 0.13 to 5.1 $\mu$mol-min$^{-1}$-mg$^{-1}$ measured with 2 mM NAD and 10 mM L-arginine methyl ester. The assay to measure the specific activity of the enzyme is described by Larew, et al. (*J. Biol. Chem.* 266: 52–57 1991). Analysis of the enzyme fraction purified on DE52 cellulose (Whatman, Maidstone, England and concanavalin A agarose, revealed a significant level of impurity as determined by sodium dodecyl sulfate-polyacrylamide gel electrophoresis (SDS-PAGE). This level of impurity was too high to permit effective amino acid sequencing as evidenced by contaminating protein of equal molecular weight. Therefore, two additional purification steps were introduced; high resolution DEAE chromatography and gel filtration-high pressure liquid chromatography (HPLC). This combination dramatically improved the purity of the transferase, as described in Example 1. The final purity was assessed by Gel filtration-HPLC (not shown). Tryptic digestion and amino acid sequencing of tryptic peptides were performed following nondenaturing gel filtration HPLC.

TABLE 1

PURIFICATION SUMMARY OF ADP-RIBOSYLTRANSFERASE FROM RABBIT SKELETAL MUSCLE

| Purification step | Protein (mg) | Units (mmol/min) | Specific activity (mmol.min$^1$.mg$^{-1}$) | Purification (-fold) | Yield (%) |
|---|---|---|---|---|---|
| 15,000 g supernatant | 26,000 | 1.70 | 0.000065 | 1 | 100 |
| KCl-washed pellet | 1,400 | 1.20 | 0.00086 | 13 | 71 |
| DE52 | 120 | 0.82 | 0.0068 | 105 | 48 |
| Concanavalin A agarose | 4 | 0.57 | 0.14 | 2,150 | 34 |
| DEAE Memsep | 0.067 | 0.29 | 4.3 | 66,150 | 17 |
| Gel filtration HPLC | 0.030 | 0.27 | 9.0 | 138,500 | 16 |
| Gel filtration HPLC (+1% SDS) | 0.005 | 0.07 | 14 | 215,400 | 4 |

While there are a variety of purification schemes that can be used to obtain the purified enzyme corresponding to the amino acid sequence of this invention, those with skill in the art will recognize that the purification scheme should maximize protein yield and maintain protein integrity thereby maximizing enzymatic activity. Following the methods disclosed in Example 1, the ADP-ribosyltransferase was purified about 215,000-fold with respect to the 15,000 g supernatant and at least 16,000-fold with respect to the membrane fraction. The overall yield, which will vary according to the methods selected, was about 4% of the starting material using the purification strategy of Example 1 (see Table 1). The specific activity of the enzyme preparation was 14 $\mu$mol-min$^{-1}$-mg$^{-1}$ when assayed with 0.1 mM NAD and 20 mM agmatine, and 68 $\mu$mol-min$^{-1}$-mg$^{-1}$ with 2 mM NAD. The transferase apparently represented approximately 90% of the purified protein.

There was a significant discrepancy between the molecular size of the transferase, estimated from the mobility of the enzyme on gel filtration-HPLC (61 kDa), and the estimated molecular size predicted from SDS-PAGE (38 kDa). This discrepancy is consistent with the interaction of the protein with CHAPS, a zwitterionic detergent (Calbiochem, La Jolla, Calif.) or alternatively with protein dimerization.

The purified enzyme preparation was subjected to tryptic digestion as described in Example 2. After running SDS-PAGE, proteins were electroblotted onto a nitrocellulose membrane and a band, corresponding to the ADP-ribosyltransferases, was excised and sent to Dr. William Lane (Harvard Microchem, Boston, Mass.). In situ tryptic digestions were performed as described (Aebersold, et al. *Proc. Natl. Acad. Sci. USA* 84: 6970–6974 (1987)). Trypsin was incubated with the piece of nitrocellulose (enzyme to substrate ratio of about 1:20). Cleaved peptides, released from the membrane, were separated by reverse-phase HPLC. Peptide-containing fractions were collected. Seven peptides, which had the highest absorption at 215 nm, were derivatized with phenylthiohydantoin and amino acid sequence analysis was performed in a gas-phase sequenator. The amino acid sequences of several tryptic peptides was determined and these are provided in Table 3 as underlined sequences. The amino acid sequence of one of the tryptic peptides of the purified ADP-ribosyltransferase (amino acids 74–87) was used to synthesize two sets of degenerate oligonucleotides, which were used as nested primers in PCR amplifications from a rabbit skeletal muscle cDNA library.

Cloning of an ADP-ribosyltransferase cDNA

As noted above, the sequence of a tryptic peptide corresponding to amino acids 74–87 in Table 3, was used to synthesize degenerate antisense oligonucleotides. Other primers, corresponding to the other tryptic peptides, could similarly be used in nested PCR reactions to identify the sequence of interest. The oligonucleotides B2, B3 and B4 (SEQ ID NOS:14–16, see also Table 2) were used in two sequential polymerase chain reactions (PCR) with oligonucleotides derived from the pBluescript plasmid sequence (BSC1, SEQ ID NO:17 and BSC2, SEQ ID NO:18, see Table 2) to identify candidate sequences from a Lambda ZAPII rabbit skeletal muscle library (see Example 2). Although both orientations of the primers were used, significant amounts of PCR product were obtained with the antisense primers (B2, B3 and B4, SEQ ID NOS: 14–16), based on amino acids 74–82, and sense plasmid primers BSC1 and BSC2, SEQ ID NOS:17 and 18, respectively. PCR fragments corresponded to the 5'-coding and untranslated region of the clone (positions –91 to 239 in Table 3). This PCR fragment was cloned into a suitable cloning vector (see Example 3) using methods well known in the art and subjected to dideoxynucleotide sequencing. Those with skill in the art will recognize that any number of commercially available cloning vectors could similarly be used to facilitate DNA sequencing. The deduced amino acid sequence of the cloned DNA fragment included a sequence that corresponded to one of the tryptic peptides (amino acids 31–58, see Table 3 and SEQ ID NO:2), thus confirming the identity of the clone.

TABLE 2

Amplification Primers

| Name | Sep. ID No. | Description |
|---|---|---|
| B2 | 14 | Inverse complement of nucleotides encoding amino acids 74–80 |
| B3 | 15 | Inverse complement of nucleotides encoding amino acids 76–82 |
| B4 | 16 | Inverse complement of nucleotides encoding amino acids 76–82 |
| BSC1 | 17 | Specific to pBluescript sequence |
| BSC2 | 18 | Specific to pBluescript sequence, 3' to BSC1 |
| TG | 19 | Inverse complement of nucleotides encoding amino acids 52–58 |
| CAU-AC | 20 | Inverse complement of nucleotides encoding amino acids 45–51 (underlined) and a subcloning sequence at 5'-end |

TABLE 2-continued

Amplification Primers

| Name | Sep. ID No. | Description |
|---|---|---|
| $R_0R_1T$ | 21 | (dT) 17 adaptor primer for 5'-RACE |
| $R_0$ | 22 | Outer adaptor primer for 5'-RACE |
| $CUA-R_1$ | 23 | Inner adaptor primer for 5'-RACE (underlined) and subcloning sequence at 5'-end |
| 5Ndel | 24 | Corresponding to amino acids 24–30 (underlined), a Ndel site (italics) plus subcloning sequence at 5'-end |
| 3BamHI | 25 | Inverse complement of nucleotides encoding amino acids 297–303 (underlined), a stop codon (double underlined), a BamHI site (italics), and a subcloning sequence at 5'-end |
| 5PRM | 26 | Inverse complement of nucleotides (–90)–(–43) |
| 48SP | 27 | Inverse complement of nucleotides encoding amino acids 31–46 |
| 3PRM | 28 | Inverse complement of nucleotides 960–1007 |
| HSM-5 | 29 | Inverse complement of nucleotides 283–306 |
| HSM-CAUN | 30 | Inverse complement of nucleotides 250–268 and contains a subcloning sequence at 5'-end |
| HSM-30 | 31 | Inverse complement of nucleotides 212–242 |
| HSM-1F | 32 | Corresponding to nucleotides 857–876 |
| CAUHSM-2F | 33 | Corresponding to nucleotides 881–901 and contains a subcloning sequence at 5'-end |
| P-RT | 34 | Inverse complement of nucleotides 1099–1122 |
| HSM-1 N | 35 | Corresponding to nucleotides (–79)–(–49) containing a subcloning sequence at 5'-end |
| HSM-RN | 36 | Inverse complement of nucleotides 1057–1074 containing a subcloning sequence at 5'-end |

Table 2 provides the sequences for the oligonucleotides that were used to identify the full length rabbit nucleic acid sequence of this invention. The letter "N" denotes any nucleotide A, C, G or T. Oligonucleotides are listed from their 5' to 3' end.

Based on the partial cDNA sequence, an oligonucleotide (48SP, SEQ ID :NO:27, see Table 2) was synthesized for use as a probe to screen a skeletal muscle cDNA library. An exemplary screening strategy is provided in Example 4. Several clones were obtained, one of which contained a sequence that overlapped with the PCR product described above. This sequence extended from position –14 to 1020 (Table 3 and SEQ ID NO:1) and contained a 981-bp open reading frame, encoding a 36, 134-kDa protein. The deduced amino acid sequence (SEQ ID NO:2, GenBank accession no. M98764) of this protein includes all seven amino acid sequences identified by tryptic digest from the purified transferase. Numbering is relative to the initiating methionine codon. Sequences identified by tryptic digest are underlined. Stop codons are double underlined. Asterisks identify potential N-glycosylation sites.

TABLE 3

Rabbit Skeletal Muscle NAD; arginine ADP - ribosyltransferan

| –105 | | GACCA | TCACATGAAG | CCAACACCAG | CTCCCCTGCC | CCGGACAAGG |
|---|---|---|---|---|---|---|
| –60 | CCTAGATGAG | GAAAGTAAGA | GTCAAAAGGA | GAGAGAAACT | GGCCTGGGGT | GGCCCCAACC |
| 1 | ATGTGGGTTC | CTGCCGTGGC | GAATCTGCTC | CTTCTGTCCC | TGGGCCTTCT | GGAAGCAATT |
| 1 | M W V | P A V A | N L L | L L S | L G L L | E A I |

TABLE 3-continued

Rabbit Skeletal Muscle NAD;
arginine ADP - ribosyltransferan

| | | | | | | |
|---|---|---|---|---|---|---|
| 61 | CAGGCCCAGA | GCCACCTGGT | CACACGTCGA | GACCTCTTCT | CTCAAGAGAC | ACCGCTGGAG |
| 21 | Q A Q | S H L V | T R R | D L F | S O E T | P L D |
| 121 | ATGGCCCCGG | CCTCCTTTGA | TGACCAGTAC | GTCGGCTGTG | CAGCAGCCAT | GACAGCTGCC |
| 41 | M A P | A S F D | D O Y | V G C | A A A M | T A A |
| 181 | CTCCCGCATC | TCAACCTCAC | GGAGTTCCAG | GTCAACAAAG | TGTATGCGGA | CGGCTGGGCA |
| 61 | L P H | L N L T | E F Q | V N K | V Y A D | G W A |
| 241 | CTGGCAAGCA | GCCAGTGGCG | GGAGCGCTCG | GCCTGGGGGC | CCGAGTGGGG | CCTCAGCACA |
| 81 | L A S | S Q W R | E R S | A W G | P E W G | L S T |
| 301 | ACCCGGCTCC | CCCCGCCGCC | TGCGGGATTT | CGGGATGAAC | ACGGGGTGGC | CCTGCTGGCC |
| 101 | T R L | P P P P | A G F | R D E | H G V A | L L A |
| 361 | TACACGGCCA | ACAGCCCCCT | ACACAAGGAG | TTCAATGCCG | CGGTACGCCA | GGCGGGCCGC |
| 121 | Y T A | N S P L | H K E | F N A | A V R Q | A G R |
| 421 | TCCCGAGCCC | ACTACCTCCA | GCACTTCTCC | TTCAAGACCC | TGCACTTCCT | GCTGACCGAG |
| 141 | S R A | H Y L Q | H F S | F K T | L H F L | L T E |
| 481 | GCCCTGCAGC | TGCTGGGCAG | GGATCAGCGA | ATGCCCAGAT | GCCGTCAGGT | GTTCCGGGGG |
| 161 | A L Q | L L G R | D Q R | M P R | C R Q V | F R G |
| 541 | GTGCATGGAC | TGCGCTTCCG | GCCAGCAGGG | CCCGGGACCA | CTGTCAGGCT | GGGGGGCTTT |
| 181 | V H G | L R F R | P A G | P G T | T V R L | G G F |
| 601 | GCCTCTGCGT | CACTGAAAAA | TGTAGCAGCC | CAGCAGTTTG | GCGAGGACAC | GTTCTTTGGC |
| 201 | A S A | S L K N | V A A | Q Q F | G E D T | F F G |
| 661 | ATCTGGACCT | GCCTTGGGGT | CCCTATCCAG | GGCTACTCCT | TTTTCCCTGG | GGAGGAGGAG |
| 221 | I W T | C L G V | P I Q | G Y S | F F P G | E E E |
| 721 | GTTCTGATCC | CCCCCTTTGA | GACCTTCCAG | GTCATCAACG | CCAGCAGACC | TGCCCAGGGC |
| 241 | V L I | P P F E | T F Q | V I N | A S F P | A Q G |
| 781 | CCTGCCCGCA | TCTACCTGAA | GGCGCTGGGC | AAGCGCAGCT | CATACAACTG | CGAGTACATC |
| 261 | P A R | I Y L K | A L G | K R S | S Y N C | E Y I |
| 841 | AAAGAAATGC | AGTGCAAGTC | TAGGCCCTGC | CACCTGGACA | ATTCAGCCTC | GGCTCAGGAG |
| 281 | K E M | Q C K S | R P C | H L D | N S A S | A Q E |
| 901 | CGCCTCTCCA | CAGCCTGGTC | CCTCCTGCTG | CTGCTCGCGT | TCCTTGCGGT | GGGGCCCTTC |
| 301 | R L S | T A W S | L L L | L L A | F L A V | G P F |
| 961 | CCAGGAAGCC | CAGGCCTCTT | CTGACCCCCC | AGACTCTGGA | CATTCCTGCC | TGCTGCCTCT |
| 321 | P G S | P G L F | End | | | |

The sequence was also obtained from poly (A)⁺RNA isolated from rabbit skeletal muscle. A preferred exemplary procedure for obtaining the sequence from poly (A)⁺RNA is provided in Example 5. The sequence of the ribosyltransferase was obtained by hybridizing primer TG, SEQ ID NO: 19 (Table 2) to the RNA to generate cDNA using an avian myeloblastosis virus (AMV) reverse transcriptase (Invitrogen, San Diego, Calif.) under conditions described by Frohman, et al. (*Proc Natl. Acad. Sci. USA* 85: 8998–9002, 1988. A 3' tail was added to the product using terminal deoxynucleotidyl transferase and the second strand was prepared by annealing primer $R_O R_I T$, SEQ ID NO:21, to the RNA and extending the primer with Taq DNA polymerase. Further amplification of the fragments, by PCR, was performed using primers TG, SEQ ID NO:19, and CAU-AC, SEQ ID NO:20, and primer pair $R_O$, SEQ ID NO:22, and CUA-$R_I$, SEQ ID NO:23. The final product was cloned into a suitable cloning vector such as pAMP1 (CloneAmp subcloning system, GIBCO-BRL, Gaithersburg, Md.) and sequenced. The sequence corresponded to positions –105 to 152 of Table 3 and was generated from 5'RACE techniques as outlined in Example 5.

Since the amino acid sequence of the N terminus of the ADP-ribosyltransferase was not identified using the techniques described above, supplemental techniques can be used to identify the position 1 methionine (Table 3 and SEQ ID NO:1). Northern analysis is used in Example 6 as one example of a method to determine the initiating methionine. The sequence of the PCR product obtained with degenerate primers B2, B3 and B4, SEQ ID NOS:14–16 (position –91 to 239) and the sequence of the 5'-RACE product (position –105 to 152) contained two in-frame stop codons upstream from the methionine codon at positions –54 to –52 and –45 to –43. Northern blot analysis indicated that oligonucleotide probes 5PRM, SEQ ID NO:26 (specific to the 5'-untranslated region, containing the two putative stop codons), 48SP, SEQ ID NO:27 (specific to the coding region) and 3PRM, SEQ ID NO:28 (specific to the 3'-end of the coding region) hybridized to RNA of the same size (about 4 kb), consistent with the conclusion that the 5'-untranslated region is present in transferase mRNA.

Once the enzyme has been cloned and sequenced it is possible to use specific probes identified from the cloned sequence, or degenerate probes with substantial homology to the cloned sequence, to assess the tissue distribution of the ADP-ribosyltransferase in other tissues (see Example 6). An ADP-ribosyltransferase specific probe was hybridized to RNA isolated from a variety of rabbit tissues. The probe recognized a 4-kb mRNA expressed primarily in skeletal and cardiac muscle tissues. The northern blots assessed the tissue distribution of the rabbit ribosyltransferase.

It is contemplated that a similar analysis could be performed on tissues derived from other vertebrates using probes derived from the rabbit ADP-ribosyltransferase sequence. Similarly, degenerate probes corresponding to the rabbit ADP-ribosyltransferase sequence, hybridization at lower temperature, washes at reduced stringencies, or the like can be used to identify ribosyltransferases from tissues of other vertebrates.

In mammals, cell lysates and partially purified protein preparations from cells indicate that arginine-specific ADP-ribosyltransferase enzymatic activity is predominantly found in skeletal muscle and cardiac tissues (Soman, et al. *Biochem. Biophys. Res. Commun.* 120: 973–980, 1984). Recently, activity was also found in murine T-cell hybridoma, thymoma and lymphoma cells (Soman, et al. *Biochem. Biophys. Res. Commun.* 176: 301–308, 1991).

The sequence and amino acid data from the ADP-ribosyltransferase facilitates an analysis of the hydrophilicity and hydrophobicity of the enzyme. This analysis helps to identify functional regions of the protein and is necessary for structurally analyzing the catalytic core of the enzyme. The hydrophilicity plot of the ribosyltransferase (FIG. 1) indicates that the enzyme has strongly hydrophobic amino and carboxyl termini and a hydrophilic center. These characteristics permit one with skill in the art to compare the functional regions of the protein with other enzymes known in the art. Here, the hydrophobic and hydrophilic pattern is common to glycophosphatidylinositol (GPI)-anchored membrane proteins (Ferguson, M.A.J. *Biochem. Soc. Trans.* 20: 243–256, 1992 and Udenfriend, et al. *Cell. Mol. Biol.* 38: 11–16, 1992). Hydrophilicity values were obtained with the MacVector program (IBI, a division of Kodak, New Haven, Connecticut) using the Kyte-Doolittle algorithm (provided in the MacVector program) using a window setting of 16 amino acids.

The hydrophobic N-terminal portion serves as a leader sequence, directing the enzyme into the endoplasmic reticulum. The hydrophobic sequence at the C terminus is recognized inside the ER as a signal for glycophosphatidylinositol modification.

Two potential sites for N-linked glycosylation were found in the deduced amino acid sequence of the transferase. These are $Asp^{65}$ and $Asp^{253}$. Since the protein binds to a lectin column (concanavalin A agarose) and because phosphatidylinositol-linked proteins are often heavily glycosylated, it is likely that the ADP-ribosyltransferase is subject to these posttranslational modifications.

To conclusively show that the cloned enzyme is an arginine-specific mono-ADP-ribosyltransferase, the sequence was cloned into a suitable expression vector and expressed in either bacteria or eukaryotes. Examples 7 and 8 outline strategies for the expression of the ADP-ribosyltransferase in *E. coli* and eukaryotic cells, respectively. Since eukaryotic cells carry endogenous levels of ADP-ribosyltransferase, the levels of enzymatic activity identified in transfected eukaryotic cells should be compared with non-transfected or mock-transfected cells.

Expression of the full length ADP-ribosyltransferase in *E. coli* was attempted using constructs of the ADP-ribosyltransferase either as a fusion protein of glutathione S-transferase or as a non-fusion protein. The protein was inactive using both constructs. ADP-ribosyltransferase activity was obtained in transformed *E. coli* using a construct that included amino acids 24–303 of the ADP-ribosyltransferase ligated as a non-fusion protein in pET3a (Novagen, Madison, Wis.). The truncated form of the protein lacked both the hydrophobic amino and carboxyl termini. In assays to assess the enzymatic activity of the protein, a product was formed that comigrated on an anion exchange HPLC column with the product (ADP-ribosylagmatine) formed by native rabbit skeletal muscle ADP-ribosyltransferase in the presence of NAD and agmatine.

In transformed rat mammary adenocarcinoma (NMU) cells transformed with the rabbit skeletal muscle ADP-ribosyltransferase cDNA seqence of SEQ ID NO: 1, significant ADP-ribosyltransferase activity was observed, with 62% occurring in the membrane fraction. ADP-ribosyltransferase activity was negligible in control NMU cells and cells transformed with either the vector alone or with the vector containing an antisense insert (Example 8).

Comparison of the Deduced Amino Acid Sequence of ADP-ribosyltransferase with Other Protein Sequences A homology search of the deduced amino acid sequence of the transferase was done at the National Center for Biotechnology Information Bethesda, Maryland using the BLAST network service. The highest homology score was obtained for rat and mouse RT6.2 protein. This protein is expressed exclusively on postthymic T cells (Koch, et al. *Proc. Natl. Acad. Sci. USA* 87: 964–967, 1990). The regions of greatest similarity were amino acids 39–88 (42% identity), 214–254 (46% identity), 107–124 (72% identity), 148–166 (52% identity) and 194–206 (61% identity). RT6.2 is a 26-kDa phosphatidylinositol-linked protein, with hydrophobic amino and carboxyl termini. The predicted amino acid sequence of the RT6.2 protein begins with a leader of 20 hydrophobic amino acids and ends with a hydrophobic stretch of 29 residues.

No significant homology was found between rabbit skeletal muscle transferase and various bacterial ADP-ribosylating toxins, the ADP-ribosyltransferase from *Rhodospirillium rubrum* or poly (ADP-ribose) polymerase. Thus, the skeletal muscle transferase is an unique enzyme, distinct from the bacterial transferases in structure and perhaps in substrate specificity.

Use of the Mammalian Sequence to Obtain Human mono-ADP ribosyltransferase

Based on the rabbit sequence provided in Table 3 and SEQ ID NO:1, two sets of nested degenerate primers were designed for use in two consecutive PCR amplifications to obtain the human ADP-ribosyltransferase sequence from isolated human skeletal muscle poly $(A)^+$RNA. Although a preferred method for isolating SEQ ID NO: 3 is provided in Example 10, other primer pairs for both 5'-RACE and 3'-RACE are contemplated including 5' GCTGTCTGCATA-CACCTGGTTGGC 3' (SEQ ID NO: 10; inverse complement of bases 80–103 in the human fragment) and 5' GTGGTTGAGATCCGGGAGAGC 3' (SEQ ID NO: 11; inverse complement of bases 47–67 in the human fragment) for 5'-RACE and 5' CCCGCATCTACCTCCGAGCC 3' (SEQ ID NO: 12; bases 54–73 in the human fragment) and 5' CAAGCACAGCACCTATAATT 3' (SEQ ID NO: 13; bases 679–698 in the human fragment). A partial cDNA sequence, encoding a 224 amino acid fragment of human skeletal muscle mono-ADP-ribosyltransferase, was obtained by PCR using primers based on the rabbit mono-ADP-ribosyltransferase sequence.

| Primers for the first PCR reaction: | |
|---|---|
| 1A: (ACGT)TT(AG)GA(TC)ATGGC(ACGT)CC(ACGT)GC | SEQ ID NO:5 |
| 1B: (ACGT)CT(ACGT)GA(TC)ATGGC(ACGT)CC(ACGT)GC | SEQ ID NO:6 |
| 2: (TC)TT(AG)CA(TC)TGCAT(TC)TC(TC)TT | SEQ ID NO:7 |
| Primers for the second PCR reaction: | |
| 3: (AGCT)TT(TC)GA(TC)GA(TC)CA(AG)TA(TC)GT | SEQ ID NO:8 |
| 4: (AGT)AT(AG)TA(TC)TC(AG)CA(AG)TT(AG)TA | SEQ ID NO:9 |

The bases in parentheses represent degenerate positions. Primers 1A and 1B correspond to amino acids 38–44 in the rabbit ADP-ribosyltransferase sequence and primer 2 is an inverse complement of nucleotides encoding amino acids 281–286. Primer 3 is internal to 1A and 1B and its sequence corresponds to amino acids 45–51. Primer 4 is internal to primer 2 and is an inverse complement of nucleotides encoding amino acids 275–280.

The resulting PCR product (about 670 base pairs) was subcloned into a vector (pAmp1, GIBCO-BRL) and sequenced by the dideoxy sequencing methods previously described. Rapid amplification of cDNA ends (RACE) was used to determine sequentially the 5' and 3' ends of the human transferase mRNA as described in Example 11. The full length human sequence (SEQ ID NO: 37) is shown in Table 4. The deduced amino acid sequence of the 224 amino acid fragment of SEQ ID NO:37, as determined from the nucleotide sequence, was 87% identical to that of the rabbit mono-ADP-ribosyltransferase (see Table 5, SEQ ID NO:4).

Completion of the Human ADP-ribosyltransferase sequence

The human ADP-ribosyltransferase sequence provided in Table 4, SEQ ID NO:3 and SEQ ID NO:4 is a partial sequence. Both the amino and carboxyl ends remain unidentified. The remaining sequence of the gene was obtained using 5'-RACE and 3'-RACE methods. These techniques are disclosed in the art and permit the rapid amplification of the 5' end and the 3' end of the cDNA. For a detailed protocol see Frohman, et al. *Technique- A Journal of Methods in Cell and Molecular Biology* 1: 165–170 1989). The 5'-RACE methodology is described in Example 5 and both the 5'-RACE and 3'-RACE methods are detailed in Example 11.

TABLE 4

NUCLEOTIDE AND DEDUCED AMINO ACID SEQUENCE OF HUMAN ADP-RIBOSYLTRANSFERSASE

TTCCACCAGG ACAGGCCTAG ATGAGGAAAC TGAGACCCAA AAAGAGACAG CAACTGGCCC 60

| AGGGTCACCA GC | ATG | CAG | ATG | CCT | GCT | ATG | ATG | TCT | CTG | CTT | CTT | GTG | 108 |
|---|---|---|---|---|---|---|---|---|---|---|---|---|---|
| | Met | Gln | Met | Pro | Ala | Met | Met | Ser | Leu | Leu | Leu | Val | |
| | 1 | | | | 5 | | | | | 10 | | | |

| TCT | GTG | GGC | CTC | ATG | GAA | GCA | CTT | CAG | GCC | CAG | AGC | CAC | CCC | ATC | ACA | 156 |
|---|---|---|---|---|---|---|---|---|---|---|---|---|---|---|---|---|
| Ser | Val | Gly | Leu | Met | Glu | Ala | Leu | Gln | Ala | Gln | Ser | His | Pro | Ile | Thr | |
| | | 15 | | | | | 20 | | | | | 25 | | | | |

| CGA | CGA | GAC | CTC | TTC | TCT | CAA | GAG | ATT | CAG | CTG | GAC | ATG | GCC | CTG | GCC | 204 |
|---|---|---|---|---|---|---|---|---|---|---|---|---|---|---|---|---|
| Arg | Arg | Asp | Leu | Phe | Ser | Gln | Glu | Ile | Gln | Leu | Asp | Met | Ala | Leu | Ala | |
| | | 30 | | | | | 35 | | | | | 40 | | | | |

| TCC | TTT | GAT | GAC | CAG | TAC | GCT | GGC | TGT | GCT | GCT | GCC | ATG | ACA | GCT | GCT | 252 |
|---|---|---|---|---|---|---|---|---|---|---|---|---|---|---|---|---|
| Ser | Phe | Asp | Asp | Gln | Tyr | Ala | Gly | Cys | Ala | Ala | Ala | Met | Thr | Ala | Ala | |
| 45 | | | | | 50 | | | | | 55 | | | | | 60 | |

| CTC | CCG | GAT | CTC | AAC | CAC | ACG | GAG | TTC | CAG | GCC | AAC | CAG | GTG | TAT | GCA | 300 |
|---|---|---|---|---|---|---|---|---|---|---|---|---|---|---|---|---|
| Leu | Pro | Asp | Leu | Asn | His | Thr | Glu | Phe | Gln | Ala | Asn | Gln | Val | Tyr | Ala | |
| | | | | 65 | | | | | 70 | | | | | 75 | | |

| GAC | AGC | TGG | ACA | CTG | GCA | AGC | AGC | CAA | TGG | CAG | GAG | CGT | CAG | GCC | AGG | 348 |
|---|---|---|---|---|---|---|---|---|---|---|---|---|---|---|---|---|
| Asp | Ser | Trp | Thr | Leu | Ala | Ser | Ser | Gln | Trp | Gln | Glu | Arg | Gln | Ala | Arg | |
| | | | 80 | | | | | 85 | | | | | 90 | | | |

| TGG | CCA | GAG | TGG | AGT | CTC | AGC | CCC | ACC | CGT | CCA | TCC | CCG | CCA | CCC | CTG | 396 |
|---|---|---|---|---|---|---|---|---|---|---|---|---|---|---|---|---|
| Trp | Pro | Glu | Trp | Ser | Leu | Ser | Pro | Thr | Arg | Pro | Ser | Pro | Pro | Pro | Leu | |
| | | 95 | | | | | 100 | | | | | 105 | | | | |

| GGC | TTC | CGC | GAT | GAG | CAT | GGG | GTG | GCC | CTC | CTG | GCC | TAC | ACA | GCC | AAC | 444 |
|---|---|---|---|---|---|---|---|---|---|---|---|---|---|---|---|---|
| Gly | Phe | Arg | Asp | Glu | His | Gly | Val | Ala | Leu | Leu | Ala | Tyr | Thr | Ala | Asn | |
| | | 110 | | | | | 115 | | | | | 120 | | | | |

| AGC | CCC | CTG | CAC | AAG | GAG | TTC | AAT | GCA | GCC | GTG | CGT | GAG | GCG | GGC | CGC | 492 |
|---|---|---|---|---|---|---|---|---|---|---|---|---|---|---|---|---|
| Ser | Pro | Leu | His | Lys | Glu | Phe | Asn | Ala | Ala | Val | Arg | Glu | Ala | Gly | Arg | |
| 125 | | | | | 130 | | | | | 135 | | | | | 140 | |

| TCC | CGG | GCC | CAC | TAC | CTC | CAC | CAC | TTC | TCC | TTC | AAG | ACA | CTC | CAT | TTC | 540 |
|---|---|---|---|---|---|---|---|---|---|---|---|---|---|---|---|---|
| Ser | Arg | Ala | His | Tyr | Leu | His | His | Phe | Ser | Phe | Lys | Thr | Leu | His | Phe | |
| | | | | 145 | | | | | 150 | | | | | 155 | | |

TABLE 4-continued

NUCLEOTIDE AND DEDUCED AMINO ACID SEQUENCE OF HUMAN ADP-RIBOSYLTRANSFERSASE

| | | | | | | | | | | | | | | | | |
|---|---|---|---|---|---|---|---|---|---|---|---|---|---|---|---|---|
| CTG | CTG | ACT | GAG | GCC | CTG | CAG | CTC | CTG | GGC | AGC | GGC | CAG | CGT | CCA | CCC | 588 |
| Leu | Leu | Thr | Glu | Ala | Leu | Gln | Leu | Leu | Gly | Ser | Gly | Gln | Arg | Pro | Pro | |
| | | | 160 | | | | 165 | | | | | 170 | | | | |
| CGG | TGC | CAC | CAG | GTG | TTC | CGA | GGT | GTG | CAC | GGC | CTG | CGC | TTC | CGG | CCA | 636 |
| Arg | Cys | His | Gln | Val | Phe | Arg | Gly | Val | His | Gly | Leu | Arg | Phe | Arg | Pro | |
| | | 175 | | | | | 180 | | | | | 185 | | | | |
| GCA | GGG | CCC | CGG | GCC | ACC | GTG | AGG | CTG | GGG | GGC | TTT | GCT | TCT | GCC | TCC | 684 |
| Ala | Gly | Pro | Arg | Ala | Thr | Val | Arg | Leu | Gly | Gly | Phe | Ala | Ser | Ala | Ser | |
| | | 190 | | | | | 195 | | | | | 200 | | | | |
| CTG | AAG | CAT | GTT | GCA | GCC | CAG | CAG | TTT | GGT | GAG | GAG | ACC | TTC | TTC | GGC | 732 |
| Leu | Lys | His | Val | Ala | Ala | Gln | Gln | Phe | Gly | Glu | Glu | Thr | Phe | Phe | Gly | |
| 205 | | | | | 210 | | | | | 215 | | | | | 220 | |
| ATC | TGG | ACC | TGC | CTT | GGG | GCC | CCT | ATC | AAG | GGC | TAC | TCC | TTC | TTC | CCT | 780 |
| Ile | Trp | Thr | Cys | Leu | Gly | Ala | Pro | Ile | Lys | Gly | Tyr | Ser | Pro | Phe | Pro | |
| | | | | 225 | | | | | 230 | | | | | 235 | | |
| GGA | GAG | GAA | GAG | GTG | CTG | ATC | CCC | CCC | TTT | GAG | ACC | TTC | CAA | GTG | ATC | 828 |
| Gly | Glu | Glu | Glu | Val | Leu | Ile | Pro | Pro | Phe | Glu | Thr | Phe | Gln | Val | Ile | |
| | | | 240 | | | | | 245 | | | | | 250 | | | |
| AAT | GCC | AGC | AGA | CCG | GCC | CAG | GGC | CCC | GCC | CGC | ATC | TAC | CTC | CGA | GCC | 876 |
| Asn | Ala | Ser | Arg | Pro | Ala | Gln | Gly | Pro | Ala | Arg | Ile | Tyr | Leu | Arg | Ala | |
| | | 255 | | | | | 260 | | | | | 265 | | | | |
| CTG | GGC | AAG | CAC | AGC | ACC | TAC | AAC | TGC | GAG | TCA | ATC | AAA | GAC | AAG | AAG | 924 |
| Leu | Gly | Lys | His | Ser | Thr | Tyr | Asn | Cys | Glu | Tyr | Ile | Lys | Asp | Lys | Lys | |
| | 270 | | | | | 275 | | | | | 280 | | | | | |
| TGC | AAG | TCT | GGG | CCT | TGC | CAT | CTG | GAT | AAT | TCA | GCC | ATG | GGT | CAG | AGC | 972 |
| Cys | Lys | Ser | Gly | Pro | Cys | His | Leu | Asp | Asn | Ser | Ala | Met | Gly | Gln | Ser | |
| 285 | | | | | 290 | | | | | 295 | | | | | 300 | |
| CCC | CTC | TCT | GCA | GTC | TGG | TCT | TTG | CTG | CTG | CTG | CTC | TGG | TTC | CTC | GTG | 1020 |
| Pro | Leu | Ser | Ala | Val | Trp | Ser | Leu | Leu | Leu | Leu | Leu | Trp | Phe | Leu | Val | |
| | | | | 305 | | | | | 310 | | | | | 315 | | |
| GTG | AGG | GCC | TTT | CCA | GAT | GGT | CCA | GGC | CTC | CTT | TGATGCATGA | GACA | | | | 1067 |
| Val | Arg | Ala | Phe | Pro | Asp | Gly | Pro | Gly | Leu | Leu | | | | | | |
| | | | 320 | | | | 325 | | | | | | | | | |

CGGGAC AGCCTCGCCTGCTG CCTCTGCCCA TCCTGAGGAT GTTGGCCATG TGTGCTTCAG 1127

TGTAACCAAG ATTCCTGTCA ATCCCATCTG CAGGGAACTC TGGGACCTTC TCTGGTAGCT 1187

GCCAGACCGG CTGGTGGAGA AACAGGAGAC AATCTGGGGA CTGAACCTTA CCCAGGGCTG 1247

TAGGAGTGAG ACTCTGAATA AAGGGTTGGG CCGGCAAAAA AAAAAAAAAA AAAAAAAA 1305

TABLE 5

COMPARISON OF AMINO ACID SEQUENCES OF MONO-ADP-RIBOSYLTRANSFERASES FROM RABBIT AND HUMAN

A: mono-ADP-ribosyltransferase from rabbit
B: residues 51-274 of mono-ADP-ribosyltransferase from human
The character to show that two aligned residues are identical is '|'

```
A  - M W V P A V A N L L L L S L G L L E A I  Q A Q S  HL V T R R D L F S Q E T P  L D MA P A S  F D D Q Y -50

A  - V G C A A A M T A A L P H L N L T E F Q V N K V Y A D G W A L A S S Q W R E R S A W G P E W G L S T -100
     | | | | | | | | | | | |   | |   | | | |   |   | | | |   |   | | | | | |   | |     | |   | | |   | |
B  - V G C A A A M T A A L P D L N H T E F Q A N Q V Y A D S W T L A S S Q W Q E R Q A R W P E W S L S P -50

A  - T R L P P P P  A G F R D E H G V A L L A Y T A N S P H L K E F N A A V R Q A G R S R A H Y L Q H F S -150
     | |     | | |    | | | | | | | | | | | | | | | | | | | | | | | |   | | | | | | | | | |   | |   | |
B  - T R P S P P P  L G F R D E H G V A L L A Y T A N S P H L K E F N A A V R E A G R S R A H Y L H H F S -100
```

TABLE 5-continued

COMPARISON OF AMINO ACID SEQUENCES OF MONO-ADP-RIBOSYLTRANSFERASES FROM RABBIT AND HUMAN

```
A  -F K T L H F L L T E A L Q L L G R D Q R MP  R C R Q V F R G V H G L R F R P  A G P  G T T  V R L G G F -200
    | | | | | | | | | | | | | | | |    | |   | | |   | | | | | | | | | | | | | | | |    | | | | | | |
B  -F K T L H F L L T E A L Q L L G S G Q R P P  R C H Q V F R G V H G L R F R P  A G P  R A T  V R L G G F -150

A  -A S A S L K N V A A Q Q F  G E D T F F G I  W T C L G V P I  Q G Y S F F P G E E E V L I  P P F E T F Q -250
    | | | | | |   | | | | | | | | | | | | | | | | | |    | |   | | | | | | | | | | | | | | | | | | | | |
B  -A S A S L K H V A A Q Q F  G E D T F F G I  W T C L G A P I  K G Y S F F P G E E E V L I  P P F E T F Q -200

A  -V I  N A S R P  A Q G P  A R I  Y L K A L G K R S S  Y N C E Y I  K E M Q C K S  R P  C H L D N S  A S  A Q E -300
    | | | | | | | | | | | | | | | | |    | | | |   |
B  -V I  N A S R P  A Q G P  A R I  Y L R A L G K H S T                                                      -224

A  -R L S T A WS L L L L L A F L A V G P  F P G S P G L F                                                    -327
```

Identity: 195 (87.1%)
Number of gaps inserted in A: 0
Number of gaps inserted in B: 0

Diagnostic Tests to Assess the Presence or Absence of ADP-ribosyltransferase Transcripts in Cell Preparations.

Northern Blots are used to detect the presence of ADP-ribosyltransferase specific transcripts in cell samples from a patient. Tissue biopsies are obtained from a patient, washed briefly in sterile saline and lysed in guanidine isothiocyanate. RNA is isolated from the lysate using commercially available kits such as the RNA isolation kits available from Invitrogen. Purified total RNA or oligo (dT) column purified mRNA is blotted onto nylon membranes in a range of from 0.05 μg to 5 μg per blot. Probes complementary to the human ADP-ribosyltransferase gene sequence such as primers 5-1 and 5-2 (see Example 11) are end labelled with $^{32}$P using polynucleotide kinase (Pharmacia) or commercially available kits. The probes are hybridized to the blotted RNA using conditions provided in Example 6 and developed at −80° C. using Kodak X-Omat film. Developed spots indicate the presence of human ADP-ribosyltransferase transcripts.

Gene Therapy using the mono-ADP-ribosyltransferase

It is contemplated that the human sequence encoding mono-ADP-ribosyltransferase can be used in a number of gene therapeutic strategies recognized in the art. For example, the full length sequence or a portion of the sequence encoding an enzymatically active fragment is incorporated into a suitable gene delivery vehicle. There are a number of gene delivery vehicles recognized in the art that are useful for delivering a gene sequence to a cell. RNA and DNA gene sequences can be incorporated into viral vectors such as retroviral vectors, influenza vectors and adenovirus vectors. Similarly, RNA and DNA gene sequences can be introduced to cells in vivo as naked gene sequences or associated with membrane fusion promoting agents such as Lipofectin®, or the like.

Introduction of the gene into patients in need of increased levels of mono-ADP-ribosyltransferase can be accommodated by in vitro gene therapy. Samples of patient cells are removed and digested into single cell suspensions. The single cell suspension is then transfected with the mono-ADP-ribosyltransferase gene that is incorporated into a suitable mammalian expression vector such as those available from Stratagene, La Jolla, Calif.; New England Biolabs, Beverly, Mass; or Promega, Madison, Wis. The expression vectors preferably contain suitable promoters such as an SV40 promoter, the Cytomegalovirus immediate early promoter, or the like, as well as a selection mechanism such as thymidine kinase or neomycin. Selection of transformants in vitro is followed by the re-introduction of the cells into, preferably, the same patient in need of increased levels of mono-ADP-ribosyltransferase.

It is additionally contemplated that antisense molecules may be prepared from the gene sequence and introduced into cells in need of ADP-ribosyltransferase down-regulation. Antisense technology is known in the art, for detailed applications of antisense technologies see U.S. Pat. No. 4,948,882 to Ruth and European Patent Publication no. EP-387775 to Beug, et al.

Mutagenesis of NAD: Arginine ADP-ribosyl transferase

The identification of the gene sequence in mammals and humans facilitates further structure/function studies to assess the interaction of the enzyme with proteins within the cell. Since the ADP-ribosyltransferases are localized within different cellular compartments, it will be possible to modify the cellular targeting of the transferase gene, through in vitro mutagenesis, and thereby alter the localization of the expressed protein and its contact with cell substrates. Transfection of mammalian cells is currently being performed in the laboratory both with intact sequence and sequence subjected to mutagenesis.

There are a variety of commercial kits available for generating site-directed mutants or random mutants of the ADP-ribosyltransferase (Bio-Rad, Richmond, Calif., Stratagene and Invitrogen, San Diego, Calif.). Once the nucleic acid sequence is incorporated into a suitable vector, the sequence is modified by oligonucleotides containing the random or site-directed mutation. Incorporation of the oligonucleotide into the unmodified sequence may occur by PCR, ligase chain reaction, single-strand mutagenesis or the like. Mutagenesis techniques are well known in the art and commercially available as kits from Bio Rad, Invitrogen, and Stratagene. These kits include extensive directions and protocols therefore no further detail is necessary to enable one with skill in the art of molecular biology to use the sequences provided herein to generate mutation in the ADP-ribosyltransferase gene.

Generation of Antibodies

ADP-ribosyltransferase gene sequence incorporated into a eukaryotic or prokaryotic expression vector is useful for generating large quantities of the enzyme that cannot otherwise be harvested easily from vertebrate tissue. Large quantities of the enzyme are useful for crystallography, for in vitro enzyme studies and for antibody preparation.

Example 11 provides methods for generating microgram/ml quantities of the enzyme that are suitable for immunization. Mice, rats or rabbits are immunized and boosted with the enzyme preparation in the presence of a suitable adjuvant such as complete or incomplete Freund's adjuvant. Polyclonal antibodies prepared by the mtthod of Example 12 and monoclonal antibodies prepared from the methods of Example 13 are used for diagnostic assays to assess the presence of the enzyme within a cell sample. Antibodies reactive with the enzyme permit the generation of enzyme linked immunosorbent assays (ELISA), western blots, and radioimmunoassays or the like. Example 13 details the production of an ELISA assay to detect the presence of ADP-ribosyltransferase in a cell sample.

Identification of other NAD: Arginine ADP-ribosyltransferase from other vertebrates:

It is contemplated that the methods disclosed herein are suitable for the isolation and sequence identification of mono-ADP-ribosyltransferase from any vertebrate. Tissue homogenates can be used to isolate intact enzyme that is purified and subjected to tryptic digestion to identify the amino acid sequence. Alternatively, RNA isolated from tissue homogenates is useful for direct identification of the ADP-ribosyltransferase sequence using degenerate primers in PCR reactions as disclosed for the human ADP-ribosyltransferase sequence.

Particular embodiments of the invention will be discussed in detail and reference will be made to possible variations within the scope of the invention. There are a variety of alternative techniques and procedures available to those of skill in the art which would similarly permit one to successfully perform the intended invention.

EXAMPLE 1

Purification of ADP-ribosyltransferase

Frozen rabbit skeletal muscle (1 kg, Pel-Freeze, Rodgers, Arkansas was thawed, ground and homogenized in a Waring blender for 1 minute at 4° C. in 3 liters of buffer A (10% sucrose/10 mM histidine, pH 7.0/1 mM EDTA/1 mM benzamidine/1 mM iodoacetamide/0.25 mM PMSF/leupeptin, pepstatin and aprotinin, each 0.5 µg/ml, Sigma, St. Louis, Mo.). The homogenate was centrifuged at 15,000 g for 30 minutes and the resulting supernatant was centrifuged at 100,000 g for 2 hours. The pellet containing 1.5 g of protein as determined by BCA protein quantitation assay (Pierce Biochemicals, Rockford, Ill.) was washed once with 400 ml of buffer B (0.6M KCl/10 mM histidine, pH 7.0/1 mM EDTA/1 mM benzamidine/1 mM iodoacetamide/0.25 mM PMSF/leupeptin, pepstatin and aprotinin, each 0.5 µg/ml) and centrifuged at 100,000 g for 1 hour. The pellet (1.4 g of protein) was suspended in 200 ml of buffer A supplemented with 0.3% sodium deoxycholate (Sigma), stirred for 30 minutes at 4° C. and centrifuged at 100,000 g for 2 hours. The supernatant, containing 0.6 g of protein was applied to a column (5×55 cm) of DE52, equilibrated with buffer C (10 mM potassium phosphate, pH 7.5/10% glycerol/0.05% sodium deoxycholate/1 mM EDTA/1 mM benzamidine).

The column was washed and eluted with a linear gradient of 0–1M NaCl in buffer C (total volume 4 liters; flow rate 6 ml/min; 20-ml fractions). Transferase activity was eluted as a single peak with maximal activity at 0.4M NaCl. Active fractions were pooled and applied to a column (1.4×4 cm) of concanavalin A agarose (Sigma) equilibrated with buffer D (50 mM Tris-Cl, pH 7.5/0.2M NaCl/1% CHAPS/0.01% NaN$_3$), followed by washing with buffer D and eluted with 25 ml of buffer D plus 0.3M methylmannopyranoside. The eluate was dialyzed at 4° C. against buffer E (10 mM Tris-Cl, pH 7.5, 1%CHAPS/0.01% NaN$_3$) and applied (4 ml/min) to a high resolution DEAE column (MemSep® cartridge, 1.4 ml bed volume, Millipore, Medford, Mass.), previously equilibrated with buffer E. After washing with buffer E, the column was eluted with a linear gradient of 0–0.3M NaCl in 60 ml of buffer E (flow rate 2 ml/min). Four 20 ml fractions that eluted at 0.025 to 0.075M NaCl and contained transferase activity were pooled and concentrated to 0.8 ml (Centricon 30 microconcentrators, Amicon, Beverly, Mass.). The resulting solution was loaded successively in 200-µl samples onto a TSK 3000 HPLC gel filtration column (TosoHaas, Philadelphia, Pa.). The column was eluted with buffer F (50 mM Tris-Cl, pH 7.0/0.2M NaCl/1% CHAPS/0.01% NaN$_3$) at a flow rate of 0.9 ml/min and 0.45-ml fractions were collected. 15-µl samples of fractions 31–41 were analyzed by SDS-PAGE in 10% acrylamide gel. Samples obtained from the HPLC gel filtration column were passed through a gel filtration column a second time in the presence of 1% SDS. 20-µl aliquots of fractions 27–35 that had passed through two gel filtration columns were analyzed by SDS-PAGE in a 12% acrylamide gel. The electrophoretic profile of the gel filtration HPLC-purified ADP-ribosyltransferase samples indicated that the second HPLC purification was useful in obtaining essentially pure ADP-ribosyltransferase. Fractions 37 and 38, containing the peak of transferase activity, were subjected to SDS-PAGE (without reducing agent). The lane corresponding to fraction 32 from the second polyacrylamide gel contained 0.1 µg of protein. Both gels were silver stained according to the methods of Rabilloud, et al. *Electrophoresis* 9: 288–291, 1988. The gel was sliced into 2-mm fragments and proteins were eluted by shaking the slices overnight at room temperature in 50 mM Tris-Cl, pH 7.5 with 1% CHAPS. Transferase activity was found in slices corresponding to the 38-kDa protein band as identified by the kDa markers used in the polyacrylamide gels. Most of the high molecular weight contaminating protein was removed by reloading the factions containing transferase activity on the same HPLC column and eluting with buffer F plus 1% SDS. Before assaying the fractions, SDS was removed by precipitation with 0.2M potassium phosphate followed by repeated concentration and dilution with buffer lacking SDS using a Centricon 30 microconcentrator.

EXAMPLE 2

Amino Acid Sequence Analysis of the ADP-ribosyltransferase

Proteins present in fractions 37 and 38 from the HPLC gel filtration protocol, in the absence of SDS, were separated by SDS-PAGE in a 10% gel and transferred to PVDF membrane. The band corresponding to the transferase (38 kDa, 10 µg of protein) was excised and subjected to in situ tryptic digestion. Peptides were HPLC-purified and seven were sequenced (Harvard Microchemistry Facility, Dr. William Lane). The procedure followed the protocol of Aebersold, et al. *Proc. Natl. Acad. Sci. USA* 84: 6970–6974, 1987. The yield of the amino acids detected in each cycle ranged from 60 pmol in early cycles to 1 pmol in later cycles. The sequences of the peptides generated from these experiments are underlined in Table 3.

EXAMPLE 3

Generation of Partial ADP-ribosyltransferase Sequences by PCR

Sequence of a tryptic peptide (amino acids 74–87) was used to synthesize degenerate antisense oligonucleotides B2, B3, and B4 (SEQ ID NOS:14–16, see Table 2). A partial cDNA sequence was generated using a nucleotide sequencing kit employing Sequenase T7 DNA polymerase (United States Biochemical, Cleveland, Ohio) in two successive polymerase chain reactions. In the first amplification, a 5-µl sample of a Lambda ZAPII (Stratagene, La Jolla, Calif.) rabbit skeletal muscle cDNA library ($8.5 \times 10^7$ pfu) was used as a template. The reaction was performed with mixed B3 and B4 primers, SEQ ID NOS:15 and 16, respectively (50 pmol of each) and BSC1 primer (SEQ ID NO:17, 10 pmol of primer, complementary to pBluescript sequence present in the Lambda ZAP vector near the cloning site). Amplification was performed in 100µl volume for 35 cycles at 94° C. for 1 minute, 57° C. for 1 minute and 72° C. for 1 minute using the PCR reagent kit with AmpliTaq DNA polymerase from Perkin-Elmer (Norwalk, Conn.). The final cycle was followed by an extension at 72°C. for 7 minutes.

The product from the first amplification (1 µl) was used as a template in a second round of PCR, together with B2 primer (SEQ ID NO:14) 50 pmol, 5' to B3 and B4 (SEQ ID NOS:15 and 16, respectively) and BSC2 primer (SEQ ID NO:18, 10 pmol, pBluescript specific, 3' to BSC1, SEQ ID NO:17). Amplification conditions were the same except for the annealing temperature, which was raised to 63° C. The major product (330-bp) was subcloned into a TA cloning plasmid vector (Invitrogen, San Diego, Calif.) and sequenced by the Sanger dideoxy chain termination method using the Sequenase sequencing kit using deoxyadenosine 5'[$\alpha$-$^{35}$s]thiotriphosphate ($^{1233}$Ci/mmol, NEN-DuPont).

EXAMPLE 4

Screening of the cDNA Library

A Lambda ZAPII rabbit skeletal muscle cDNA library (Stratagene, $1.7 \times 10^{10}$ pfu/ml) was screened in *E. coli* XL-1 Blue host cells (Stratagene) by plaque hybridization (about $5 \times 10^5$ plaques) with the 48SP oligonucleotide probe, SEQ ID NO:27, labeled with [$\alpha$-$^{32}$-P] dATP (New England Nuclear, Beverly, Mass.) and terminal deoxynucleotidyl transferase (GIBCO-BRL, Gaithersburg, Md.) to a specific activity of $5 \times 10^7$ cpm/pmol. Duplicate lifts of 2 minutes and 4 minutes were performed using nylon colony/plaque hybridization filters. Filters were prehybridized for 4 hours at 42° C. in 5×SSC (1×SSC=0.15M NaCl/0.015M sodium citrate, pH 7.0), 5× Denhardt's solution (1×=0.02% Ficol, 0.02% polyvinylpyrrolidone,0.02% bovine serum albumin), 10 mM Tris-Cl (pH 7.4), 10% dextran sulfate, 0.5% SDS and salmon sperm DNA (100 µg/ml, Lofstrand Laboratories, Gaithersburg, Md.). Hybridization was performed in the same solution, supplemented with radiolabeled probe ($2 \times 10^6$ cpm/filter). Filters were washed twice in 2×SSC/ 0.5% SDS at room temperature and twice in 0.5×SSC/0.5% SDS at 42° C. and exposed to Kodak X-OMAT film for 24 hours at –80° C. with intensifying screens. After three rounds of screening, several positive clones were identified. pBluescript plasmids carrying the cloned cDNA insert were excised in vivo, purified, and sequenced.

EXAMPLE 5

Rapid Amplification of 5'-end of cDNA (5'-RACE)

Amplification was performed as described (Frohman, et al. *Proc. Natl. Acad. Sci. USA* 85: 8998–9002 1988 with some modifications. Poly (A)$^+$RNA from rabbit skeletal muscle was denatured with methyl mercury hydroxide and the first cDNA strand was synthesized by extension of primer TG, SEQ ID NO:19 (Table 2) with AMV reverse transcriptase (Invitrogen). After 3'-end tailing of the product with dATP and terminal deoxynucleotidyl transferase, the second cDNA strand was synthesized by annealing and extending primer $R_OR_JT$, SEQ ID NO:21 with Taq DNA polymerase. Two rounds of PCR amplifications were then performed using primers TG, SEQ ID NO:19 and CAU-AC, SEQ ID NO:20, on one side of the cDNA fragment and $R_O$, SEQ ID NO:22 and CUA-$R_J$, SEQ ID NO:23 on the other side. The final product was subcloned into the pAMP1 vector using the CloneAmp system (GIBCO-BRL) and sequenced.

EXAMPLE 6

Northern Blot Analysis

Total RNA was isolated from rabbit tissues as described by Chomczynski and Sacchi (*Anal. Biochem.* 162: 156–159, 1987). Poly (A)$^+$RNA was purified from total RNA using oligo(dT) columns (Clontech, Palo Alto, Calif.). For Northern blot analysis, 20–30 µg of total RNA or 5 µg of poly(A)$^+$RNA was subjected to electrophoresis in a denaturing 1.2% agarose gel containing formaldehyde and ethidium bromide and then transferred to Nytran membrane. After prehybridization for 12 hours at 42° C. in 5×SSC/10× Denhardt's reagent/40% formamide/0.1% SDS/10% dextran sulfate/and 100 µg/ml of salmon sperm DNA, hybridization was performed for 16 hours at 42° C. in 5×SSC/2× Denhardt's/40% formamide/3% SDS/10% dextran sulfate/ 100 µg/ml of salmon sperm DNA and an oligonucleotide probe ($2 \times 10^6$ cpm/ml), radiolabeled as described in Example 4. Blots were washed twice in 2×SSC/0.1% SDS and once in 0.5×SSC/0.1% SDS at room temperature and once in 0.1 ×SSC/0.1% SDS at 60° C. and exposed to Kodak X-OMAT film at –80° C. for 24 hours with intensifying screens. Transferase specific probe 5PRM, SEQ ID NO:26 (see Table 2 for probe sequence) was specific to the 5'-untranslated region of the cDNA; Probe 48SP, SEQ ID NO:27, was specific to the coding region; and probe 3PRM, SEQ ID NO:28, was specific to the 3'-end of the coding region.

This procedure was also used to assess the distribution of ADP-ribosyltransferase specific RNA in different tissues. These tissues included skeletal muscle, smooth muscle, heart, brain, lung, kidney, spleen and liver. 20–30 µg of total RNA from the indicated tissues were hybridized with the transferase-specific probe, 48SP, SEQ ID NO:27. Total RNA was visualized on the gel following ethidium bromide staining using UV transillumination.

EXAMPLE 7

Expression of ADP-ribosyltransferase in *E. coli*

ADP-ribosyltransferase cDNA was amplified by PCR using the primers 5Ndel, SEQ ID NO:24 and 3BamHI, SEQ ID NO:25. The PCR product was gel-purified, digested with Ndel and BamHI restriction enzymes (Promega) and the resulting 875-bp fragment was ligated to Ndel- and BamHI-digested pET3a (Novagen) with T4 DNA ligase (Promega) at 16° C. for 16 hours. BL21 (DE3) cells (Novagen) were transformed with the ligation product and applied to LB/ampicillin plates. After incubation overnight at 37° C., colonies were screened by hybridization with the 48SP oligonucleotide probe, SEQ ID NO:27. One positive colony was grown at 37° C. for 4 hours in LB/ampicillin medium. The culture was then diluted 1:10 in 5 ml of the same medium, grown for 1 hour and induced with 0.4 mM IPTG (isopropyl-β-D-thiogalactopyranoside) for 1.5 hours. After centrifugation at 10,000 g for 2 minutes the pellet was dispersed in 10 mM Tris-Cl, pH 8.0/1 mM EDTA/0.5 mM PMSF/leupeptin, aprotinin and pepstatin, each 0.5 µg/ml. Following a 30s sonication on ice, samples were used for SDS-PAGE or transferase assay.

Protein concentration was determined either by BCA assay or ISS protein gold (Integrated Protein Systems, Natick, Mass.) with bovine serum albumin as the standard. SDS-polyacrylamide gels were stained with Coomassie Blue or with silver stain (Rabilloud, et al., supra).

EXAMPLE 8

Expression of ADP-ribosyltransferase in mammalian cells

Rat mammary adenocarcinoma (NMU) cells were grown in Eagle's Modified Essential Medium (EMEM) containing 10% fetal calf serum. Subconfluent NMU cells on 100×20 mm dishes were transformed with 15 µg of purified pMAMneo (Higuchi, (1989) in PCR Technology: Principles and Applications for DNA Amplification, Ehrlich, H. A., ed., pp. 61–70, Stockton press, New York), pM-T, pM-AT or pM-3'T constructs by the calcium phosphate precipitation method (Ausubel et al., (1990) Current Protocols in Molecular Biology, Vol. I, p. 9.1.1., John Wiley & Sons, New York).

To generate the pM-T construct, NheI and XhoI restriction sites were added to the 5' and 3' ends, respectively, of the rabbit skeletal muscle ADP-ribosyltransferase cDNA during PCR amplification for ligation into pMAMneo. The PCR product and pMAMneo vector were digested with NheI and XhoI and ligated using T4 DNA ligase. In the pM-AT construct, the ADP-ribosyltransferase cDNA was ligated into the pMAMneo vector in the reverse orientation. To generate the pM-3'T construct, the truncated form of the ADP-ribosyltransferase, from which 75 bases were removed at the 3'-end of the cDNA coding region, was cloned into pMAMneo. All cloning steps were methods well known in the art.

Cells were allowed to double before plating in selective medium (EMEM containing 10% FCS and 500 µg/ml G418). Expression of stably incorporated ADP-ribosyltransferase was induced by incubation of cells with 1 µM dexamethasone sodium phosphate for 48 hours (Sardet et al., (1989) Cell, 56: 271–280).

EXAMPLE 9

Assay to Detect ADP-ribosyltransferase Activity

ADP-ribosyltransferase activity was assayed in 300 µl of 50 mM potassium phosphate, pH 7.5, with 20 mM agmatine (Sigma, St. Louis, Mo.) and 0.1 mM [adenine-U-$^{14}$C]NAD (1.7 mCi/mmol) (Amersham, Arlington Heights, Ill.) and cold NAD (Sigma). After incubation at 30° C., a 100-µl sample was applied to a 1-ml column of Dowex AG 1-X2 (Bio-Rad, Richmond, Calif.). [$^{14}$C]ADP-ribosylagmatine was eluted with 5 ml of $H_2O$ for radioassay. The elution profiles of [$^{14}$C]ADP-ribosylagmatine with 0.1M sodium phosphate, pH 4.5 (flow rate 1 ml/minute) after incubation with native transferase, recombinant enzyme or control E. coli cells, transformed with expression vector lacking insert, with 0.1 mM [adenine-U-$^{14}$C]NAD or without or with 20 mM agmatine. The elution times for adenosine, nicotinamide (Nic) and NAD did not vary between the native and recombinant enzyme.

EXAMPLE 10

Identification of the Human mono-ADP-ribosyltransferase sequence

Human skeletal muscle mRNA (0.5 µg, Clontech) was reverse transcribed (Invitrogen) using a mixed oligo(dT) primer (0.2 µg) and random hexamer primers (1 µg) (total volume 20 µl) (Invitrogen). Techniques for isolating mRNA are disclosed in Example 6. The first strand of cDNA was used as a template in a PCR reaction employing mixed primers 1A, 1B and 2, SEQ ID NOS:5–7, (50 pmol of each). Amplification products (1% of the reaction volume) were reamplified in a second PCR reaction, using primers 3 and 4, SEQ ID NOS 8 and 9, respectively (50 pmol of each). Both PCR amplifications were performed under the same conditions (35 cycles of 94° C. for one minute, 72° for two minutes; followed by extension at 72° for 7 minutes).

EXAMPLE 11

Completion of the Human ADP-ribosyltransferase Sequence

The fragment of human ADP-ribosyltransferase as provided in Table 5 and SEQ ID NO:3 consisted of 224 amino acids. The full length nascent protein is likely to be about 330 amino acids long. It was estimated that about 70% of the human sequence was known and about 30% of the sequence still remained to be identified. The 5' and 3' remaining portions of the sequence were identified using 5'-RACE and 3'-RACE methods (rapid amplifications of 5'-end and 3'-end of cDNA, respectively) see Frohman, et al. *Technique- A Journal of Methods in Cell and Molecular Biology* 1: 165–170 (1989). These procedures are easily performed by those skilled in the art and are used routinely in our laboratory. One example of the 5'-RACE methodology is provided in Example 5.

Human skeletal muscle poly(A)$^+$RNA (1 µg) was denatured with methylmercury hydroxide and reverse transcribed with MoMLV reverse transcriptase and 100 ng of transferase-specific primers; HSM-5 for 5'RACE (SEQ ID NO: 29), and $R_O$ primer (SEQ ID NO: 22) for 3'-RACE.

The first cDNA strand product from the 5' end was incubated with dATP and terminal deoxynucleotidyl transferase to add a 3' deoxyadenosine tail as described (Frohman and Martin, 1989). The second DNA strand was synthesized using 100 ng of primers $R_O$ (SEQ ID NO: 22) and $R_OR_IT$ (SEQ ID NO: 21) with Taq DNA polymerase according to the GeneAmp PCR Kit protocol (Perkin-Elmer, Norwalk, Conn.). Amplification was performed for 30 cycles at 94° C. for 1 minute; 72° C. for 2 minutes followed by a 7 minute extension at 72° C. The 50 µl reaction mix was diluted to 1 ml with TE buffer (10 mM Tris-HCl, pH 7.5, 1 mM EDTA) and the PCR product was separated from the primers using a Centricon 100 microconcentrator (Amicon, Beverly, Mass.). A second amplification was performed with 1 µl of the first amplification product as a template, and 100 ng of nested primers HSM-CAUN (SEQ ID NO: 30) and HSM-30 (SEQ ID NO: 31). Reaction conditions were the same as above. The PCR product was ethanol precipitated and 5'-phosphorylated using T4 polynucleotide kinase (1 µl; Promega, Madison, Wis.) according to the manufacturer's protocol. The phosphorylated product was analyzed by electrophoresis on a low melting point 1% agarose gel, excised from the gel and subcloned into the pGEM-72(+) cloning vector (Promega, Madison, Wis.). Plasmid DNA was purified and sequenced as described previously.

The first cDNA strand from the 3' cDNA end was amplified by PCR using primers $R_O$ (SEQ ID NO: 22) and HSM-1F (SEQ ID NO: 32). After separating the PCR product from the primers, a second round of amplification was performed using primers CAUHSM-2F (SEQ ID NO: 33) and CUA-RI (SEQ ID NO: 23). Amplification conditions were identical to those for the 5'-RACE procedure, except that the reaction was continued for 35 cycles instead of 30. The amplified product was cloned into the pAMP1 vector using the CloneAmp system and sequenced.

To confirm the sequence of the entire human skeletal muscle transferase cDNA, poly(A)+RNA (1 μg) was reverse transcribed as described above using primer P-RT (SEQ ID NO: 34) followed by two rounds of PCR amplification using primers HSM-1 and HSM-3 and subsequently nested primers HSM-1N (SEQ ID NO: 35) and HSM-RN (SEQ ID NO: 36). The final PCR product was subcloned and sequenced.

EXAMPLE 12

Preparation of anti-ADP-ribosyltransferase antibodies

A truncated form of the rabbit muscle transferase lacking the hydrophobic amino- and carboxy-termini was expressed as a non-fusion protein in *E. coli* as described (Zolkiewska et al., (1992) *Proc. Natl. Acad. Sci. U.S.A.*, 89: 11352–11356). Expression of the transferase was induced with isopropylthiogalactoside (IPTG) in a 20 ml suspension of *E. coli*. The suspension was sonified followed by the addition of 1% CHAPS, then centrifuged at 14,000×g for 5 minutes. The pellet, containing 500 μg protein, was emulsified in 1 ml of PBS and 1 ml of Freund's complete adjuvant and injected subcutaneously into rabbits having a body weight of 1–1.5 kg. Rabbits were injected every two weeks with transferase emusified in Freund's incomplete adjuvant. The rabbits were bled after the fourth injection and antibody titer was assessed against ADP-ribosyltransferase on Western blots.

EXAMPLE 13

ELISA assay to Detect the Presence of ADP-ribosyltransferase in a Cell Sample Techniques for generating monoclonal antibodies are well known in the art. For a review of monoclonal antibody production, selection and screening see Davis, et al. *Basic Methods in Molecular Biology*. 1986. Elsevier Press, N.Y. pp. 348–354. Briefly, the purified protein preparation (50 μg per injection) of Example 1 or Example 7 is combined with an equal volume of complete freund's adjuvant. The remaining injections use between 20–50 μg purified protein per injection with an equal volume of incomplete freund's adjuvant. Injections are given to the mice at weekly intervals for approximately 6 weeks.

The spleens are removed, teased and the splenocytes are isolated. Erythrocytes are lysed and the mouse splenocytes are mixes at a cell ratio of 4 spleen cells to 1 myeloma cell (cell line SP2/0, or the like, American type Culture Collection, Rockville, Md.). 50% polyethyleneglycol is added to the cell pellet containing the myeloma and splenocytes slowly over 1 minute. This is followed with 1 ml of cell culture medium. Cells are selected in hypoxanthine, aminopterin and thymidine as described by Davis, et al. (supra). Positive colonies are screened by ELISA. Antibody produced by these methods is purified using column chromatography, ammonium sulphate cuts or other methods known in the art of immunology.

ELISA strategies are well known in the art. As one preferred example of an ELISA assay, 200 μg of purified protein at 1 μg/ml. in phosphate buffered saline (PBS) is incubated in each well of a 96 well ELISA plate overnight at 4° C. The wells are washed with PBS containing 0.05% Tween 20. Media from the cell fusions, mouse or patient sera is serially diluted 1:5 in PBS containing 0.05% Tween 20 and Bovine Serum Albumin (0.1 mg/ml) in serial dilutions. 200 μl of each dilution are added in duplicate to the 96 well plate. Controls are added as well. Plates are incubated for 1 hr at room temperature and the wells are washed in PBS containing Tween, as described above. Aliquots of goat anti-mouse or human IgG conjugated to alkaline phosphatase diluted 1:400 in PBS containing Tween is added to each well. Plates are incubated for 1 hr at room temperature. Following a wash step, 200 μl of a suitable chromogenic substrate are added with hydrogen peroxide according to directs contained in the substrate. Color development indicative of the presence of antibody to the purified protein in monitored on an ELISA reader.

While particular embodiments of the invention have been described in detail, it will be apparent to those skilled in the art that these embodiments are exemplary rather than limiting, and the true scope of the invention is that defined in the following claims.

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 1140 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: CDS
    ( B ) LOCATION: 106..1086

( x i ) SEQUENCE DESCRIPTION: SEQ ID NO:1:

```
GACCATCACA TGAAGCCAAC ACCAGCTCCC TTGCCCCGGA CAAGGCCTAG ATGAGGAAAG           60

TAAGAGTCAA AAGGAGAGAG AAACTGGCCT GGGGTGGCCC CAACC ATG TGG GTT             114
                                                   Met Trp Val
                                                    1

CCT GCC GTG GCG AAT CTG CTC CTT CTG TCC CTG GGC CTT CTG GAA GCA           162
Pro Ala Val Ala Asn Leu Leu Leu Leu Ser Leu Gly Leu Leu Glu Ala
      5              10                  15

ATT CAG GCC CAG AGC CAC CTG GTC ACA CGT CGA GAC CTC TTC TCT CAA           210
Ile Gln Ala Gln Ser His Leu Val Thr Arg Arg Asp Leu Phe Ser Gln
 20              25                  30                      35

GAG ACA CCG CTG GAC ATG GCC CCG GCC TCC TTT GAT GAC CAG TAC GTC           258
Glu Thr Pro Leu Asp Met Ala Pro Ala Ser Phe Asp Asp Gln Tyr Val
                  40                  45                  50

GGC TGT GCA GCA GCC ATG ACA GCT GCC CTC CCG CAT CTC AAC CTC ACG           306
Gly Cys Ala Ala Ala Met Thr Ala Ala Leu Pro His Leu Asn Leu Thr
              55                  60                  65

GAG TTC CAG GTC AAC AAA GTG TAT GCG GAC GGC TGG GCA CTG GCA AGC           354
Glu Phe Gln Val Asn Lys Val Tyr Ala Asp Gly Trp Ala Leu Ala Ser
          70                  75                  80

AGC CAG TGG CGG GAG CGC TCG GCC TGG GGG CCC GAG TGG GGC CTC AGC           402
Ser Gln Trp Arg Glu Arg Ser Ala Trp Gly Pro Glu Trp Gly Leu Ser
      85                  90                  95

ACA ACC CGG CTC CCC CCG CCG CCT GCG GGA TTT CGG GAT GAA CAC GGG           450
Thr Thr Arg Leu Pro Pro Pro Pro Ala Gly Phe Arg Asp Glu His Gly
100             105                 110                 115

GTG GCC CTG CTG GCC TAC ACG GCC AAC AGC CCC CTA CAC AAG GAG TTC           498
Val Ala Leu Leu Ala Tyr Thr Ala Asn Ser Pro Leu His Lys Glu Phe
                120                 125                 130

AAT GCC GCG GTA CGC CAG GCG GGC CGC TCC CGA GCC CAC TAC CTC CAG           546
Asn Ala Ala Val Arg Gln Ala Gly Arg Ser Arg Ala His Tyr Leu Gln
            135                 140                 145

CAC TTC TCC TTC AAG ACC CTG CAC TTC CTG CTG ACC GAG GCC CTG CAG           594
His Phe Ser Phe Lys Thr Leu His Phe Leu Leu Thr Glu Ala Leu Gln
        150                 155                 160

CTG CTG GGC AGG GAT CAG CGA ATG CCC AGA TGC CGT CAG GTG TTC CGG           642
Leu Leu Gly Arg Asp Gln Arg Met Pro Arg Cys Arg Gln Val Phe Arg
    165                 170                 175

GGG GTG CAT GGA CTG CGC TTC CGG CCA GCA GGG CCC GGG ACC ACT GTC           690
Gly Val His Gly Leu Arg Phe Arg Pro Ala Gly Pro Gly Thr Thr Val
180             185                 190                 195

AGG CTG GGG GGC TTT GCC TCT GCG TCA CTG AAA AAT GTA GCA GCC CAG           738
Arg Leu Gly Gly Phe Ala Ser Ala Ser Leu Lys Asn Val Ala Ala Gln
                200                 205                 210

CAG TTT GGC GAG GAC ACG TTC TTT GGC ATC TGG ACC TGC CTT GGG GTC           786
Gln Phe Gly Glu Asp Thr Phe Phe Gly Ile Trp Thr Cys Leu Gly Val
            215                 220                 225

CCT ATC CAG GGC TAC TCC TTT TTC CCT GGG GAG GAG GAG GTT CTG ATC           834
Pro Ile Gln Gly Tyr Ser Phe Phe Pro Gly Glu Glu Glu Val Leu Ile
        230                 235                 240

CCC CCC TTT GAG ACC TTC CAG GTC ATC AAC GCC AGC AGA CCT GCC CAG           882
Pro Pro Phe Glu Thr Phe Gln Val Ile Asn Ala Ser Arg Pro Ala Gln
    245                 250                 255

GGC CCT GCC CGC ATC TAC CTG AAG GCG CTG GGC AAG CGC AGC TCA TAC           930
Gly Pro Ala Arg Ile Tyr Leu Lys Ala Leu Gly Lys Arg Ser Ser Tyr
```

```
                    260                      265                      270                      275
AAC  TGC  GAG  TAC  ATC  AAA  GAA  ATG  CAG  TGC  AAG  TCT  AGG  CCC  TGC  CAC              978
Asn  Cys  Glu  Tyr  Ile  Lys  Glu  Met  Gln  Cys  Lys  Ser  Arg  Pro  Cys  His
                    280                      285                      290

CTG  GAC  AAT  TCA  GCC  TCG  GCT  CAG  GAG  CGC  CTC  TCC  ACA  GCC  TGG  TCC             1026
Leu  Asp  Asn  Ser  Ala  Ser  Ala  Gln  Glu  Arg  Leu  Ser  Thr  Ala  Trp  Ser
               295                      300                      305

CTC  CTG  CTG  CTG  CTC  GCG  TTC  CTT  GCG  GTG  GGG  CCC  TTC  CCA  GGA  AGC             1074
Leu  Leu  Leu  Leu  Leu  Ala  Phe  Leu  Ala  Val  Gly  Pro  Phe  Pro  Gly  Ser
          310                      315                      320

CCA  GGC  CTC  TTC  TGACCCCCCA  GACTCTGGAC  ATTCCTGCCT  GCTGCCTCTG                          1126
Pro  Gly  Leu  Phe
     325

CCCACTCTGT  GGAT                                                                            1140
```

( 2 ) INFORMATION FOR SEQ ID NO:2:

( i ) SEQUENCE CHARACTERISTICS:
        ( A ) LENGTH: 327 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Trp  Val  Pro  Ala  Val  Ala  Asn  Leu  Leu  Leu  Ser  Leu  Gly  Leu
 1                   5                   10                       15

Leu  Glu  Ala  Ile  Gln  Ala  Gln  Ser  His  Leu  Val  Thr  Arg  Arg  Asp  Leu
                    20                       25                       30

Phe  Ser  Gln  Glu  Thr  Pro  Leu  Asp  Met  Ala  Pro  Ala  Ser  Phe  Asp  Asp
               35                       40                       45

Gln  Tyr  Val  Gly  Cys  Ala  Ala  Met  Thr  Ala  Ala  Leu  Pro  His  Leu
          50                        55                       60

Asn  Leu  Thr  Glu  Phe  Gln  Val  Asn  Lys  Val  Tyr  Ala  Asp  Gly  Trp  Ala
 65                       70                       75                       80

Leu  Ala  Ser  Ser  Gln  Trp  Arg  Glu  Arg  Ser  Ala  Trp  Gly  Pro  Glu  Trp
               85                        90                       95

Gly  Leu  Ser  Thr  Thr  Arg  Leu  Pro  Pro  Pro  Ala  Gly  Phe  Arg  Asp
               100                      105                      110

Glu  His  Gly  Val  Ala  Leu  Leu  Ala  Tyr  Thr  Ala  Asn  Ser  Pro  Leu  His
               115                      120                      125

Lys  Glu  Phe  Asn  Ala  Ala  Val  Arg  Gln  Ala  Gly  Arg  Ser  Arg  Ala  His
          130                      135                      140

Tyr  Leu  Gln  His  Phe  Ser  Phe  Lys  Thr  Leu  His  Phe  Leu  Leu  Thr  Glu
145                      150                      155                      160

Ala  Leu  Gln  Leu  Leu  Gly  Arg  Asp  Gln  Arg  Met  Pro  Arg  Cys  Arg  Gln
               165                      170                      175

Val  Phe  Arg  Gly  Val  His  Gly  Leu  Arg  Phe  Arg  Pro  Ala  Gly  Pro  Gly
          180                      185                      190

Thr  Thr  Val  Arg  Leu  Gly  Gly  Phe  Ala  Ser  Ala  Ser  Leu  Lys  Asn  Val
          195                      200                      205

Ala  Ala  Gln  Gln  Phe  Gly  Glu  Asp  Thr  Phe  Phe  Gly  Ile  Trp  Thr  Cys
210                      215                      220

Leu  Gly  Val  Pro  Ile  Gln  Gly  Tyr  Ser  Phe  Phe  Pro  Gly  Glu  Glu
225                      230                      235                      240

Val  Leu  Ile  Pro  Pro  Phe  Glu  Thr  Phe  Gln  Val  Ile  Asn  Ala  Ser  Arg
                    245                      250                      255
```

| | | | | | | | | | | | | | | | |
|---|---|---|---|---|---|---|---|---|---|---|---|---|---|---|---|
| Pro | Ala | Gln | Gly<br>260 | Pro | Ala | Arg | Ile<br>265 | Tyr | Leu | Lys | Ala | Leu<br>270 | Gly | Lys | Arg |
| Ser | Ser | Tyr<br>275 | Asn | Cys | Glu | Tyr | Ile<br>280 | Lys | Glu | Met | Gln | Cys<br>285 | Lys | Ser | Arg |
| Pro | Cys<br>290 | His | Leu | Asp | Asn | Ser<br>295 | Ala | Ser | Ala | Gln | Glu<br>300 | Arg | Leu | Ser | Thr |
| Ala<br>305 | Trp | Ser | Leu | Leu | Leu<br>310 | Leu | Leu | Ala | Phe | Leu<br>315 | Ala | Val | Gly | Pro | Phe<br>320 |
| Pro | Gly | Ser | Pro | Gly<br>325 | Leu | Phe | | | | | | | | | |

(2) INFORMATION FOR SEQ ID NO:3:

(i) SEQUENCE CHARACTERISTICS:
        (A) LENGTH: 669 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (v) FRAGMENT TYPE: internal (ix) FEATURE:
        (A) NAME/KEY: CDS
        (B) LOCATION: 1..669

(xi) SEQUENCE DESCRIPTION: SEQ ID NO:3:

| | | | | | | | | | | | | | | | | |
|---|---|---|---|---|---|---|---|---|---|---|---|---|---|---|---|---|
| GGC | TGT | GCT | GCT | GCC | ATG | ACA | GCT | GCT | CTC | CCG | GAT | CTC | AAC | CAC | ACG | 48 |
| Gly<br>1 | Cys | Ala | Ala | Ala<br>5 | Met | Thr | Ala | Ala | Leu<br>10 | Pro | Asp | Leu | Asn | His<br>15 | Thr | |
| GAG | TTC | CAG | GCC | AAC | CAG | GTG | TAT | GCA | GAC | AGC | TGG | ACA | CTG | GCA | AGC | 96 |
| Glu | Phe | Gln | Ala<br>20 | Asn | Gln | Val | Tyr | Ala<br>25 | Asp | Ser | Trp | Thr | Leu<br>30 | Ala | Ser | |
| AGC | CAA | TGG | CAG | GAG | CGT | CAG | GCC | AGG | TGG | CCA | GAG | TGG | AGT | CTC | AGC | 144 |
| Ser | Gln | Trp<br>35 | Gln | Glu | Arg | Gln | Ala<br>40 | Arg | Trp | Pro | Glu | Trp<br>45 | Ser | Leu | Ser | |
| CCC | ACC | CGT | CCA | TCC | CCG | CCA | CCC | CTG | GGC | TTC | CGC | GAT | GAG | CAT | GGG | 192 |
| Pro | Thr<br>50 | Arg | Pro | Ser | Pro | Pro<br>55 | Pro | Leu | Gly | Phe | Arg<br>60 | Asp | Glu | His | Gly | |
| GTG | GCC | CTC | CTG | GCC | TAC | ACA | GCC | AAC | AGC | CCC | CTG | CAC | AAG | GAG | TTC | 240 |
| Val<br>65 | Ala | Leu | Leu | Ala | Tyr<br>70 | Thr | Ala | Asn | Ser | Pro<br>75 | Leu | His | Lys | Glu | Phe<br>80 | |
| AAT | GCA | GCC | GTG | CGT | GAG | GCG | GGC | CGC | TCC | CGG | GCC | CAC | TAC | CTC | CAC | 288 |
| Asn | Ala | Ala | Val | Arg<br>85 | Glu | Ala | Gly | Arg | Ser<br>90 | Arg | Ala | His | Tyr | Leu<br>95 | His | |
| CAC | TTC | TCC | TTC | AAG | ACA | CTC | CAT | TTC | CTG | CTG | ACT | GAG | GCC | CTG | CAG | 336 |
| His | Phe | Ser | Phe<br>100 | Lys | Thr | Leu | His | Phe<br>105 | Leu | Leu | Thr | Glu | Ala<br>110 | Leu | Gln | |
| CTC | CTG | GGC | AGC | GGC | CAG | CGT | CCA | CCC | CGG | TGC | CAC | CAG | GTG | TTC | CGA | 384 |
| Leu | Leu | Gly<br>115 | Ser | Gly | Gln | Arg | Pro<br>120 | Pro | Arg | Cys | His | Gln<br>125 | Val | Phe | Arg | |
| GGT | GTG | CAC | GGC | CTG | CGC | TTC | CGG | CCA | GCG | GGG | CCC | CGG | GCC | ACC | GTG | 432 |
| Gly | Val | His<br>130 | Gly | Leu | Arg | Phe | Arg<br>135 | Pro | Ala | Gly | Pro<br>140 | Arg | Ala | Thr | Val | |
| AGG | TTG | GGG | GGC | TTT | GCT | TCT | GCC | TCC | CTG | AAG | CAT | GTT | GCA | GCC | CAG | 480 |
| Arg<br>145 | Leu | Gly | Gly | Phe | Ala<br>150 | Ser | Ala | Ser | Leu | Lys<br>155 | His | Val | Ala | Ala | Gln<br>160 | |
| CAG | TTT | GGT | GAG | GAC | ACC | TTC | TTC | GGC | ATC | TGG | ACC | TGC | CTT | GGG | GCC | 528 |
| Gln | Phe | Gly | Glu | Asp | Thr | Phe | Phe | Gly | Ile | Trp | Thr | Cys | Leu | Gly | Ala | |

```
                              165                        170                         175
CCT  ATC  AAG  GGC  TAC  TCC  TTC  TTC  CCT  GGA  GAG  GAA  GAG  GTG  CTG  ATC        576
Pro  Ile  Lys  Gly  Tyr  Ser  Phe  Phe  Pro  Gly  Glu  Glu  Glu  Val  Leu  Ile
               180                        185                        190

CCC  CCC  TTT  GAG  ACC  TTC  CAA  GTG  ATC  AAT  GCC  AGC  AGA  CCG  GCC  CAG        624
Pro  Pro  Phe  Glu  Thr  Phe  Gln  Val  Ile  Asn  Ala  Ser  Arg  Pro  Ala  Gln
          195                        200                        205

GGC  CCC  GCC  CGC  ATC  TAC  CTC  CGA  GCC  CTG  GGC  AAG  CAC  AGC  ACC             669
Gly  Pro  Ala  Arg  Ile  Tyr  Leu  Arg  Ala  Leu  Gly  Lys  His  Ser  Thr
     210                        215                        220
```

( 2 ) INFORMATION FOR SEQ ID NO:4:

( i ) SEQUENCE CHARACTERISTICS:
        ( A ) LENGTH: 223 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Gly  Cys  Ala  Ala  Ala  Met  Thr  Ala  Ala  Leu  Pro  Asp  Leu  Asn  His  Thr
 1                   5                        10                        15

Glu  Phe  Gln  Ala  Asn  Gln  Val  Tyr  Ala  Asp  Ser  Trp  Thr  Leu  Ala  Ser
               20                        25                        30

Ser  Gln  Trp  Gln  Glu  Arg  Gln  Ala  Arg  Trp  Pro  Glu  Trp  Ser  Leu  Ser
          35                        40                        45

Pro  Thr  Arg  Pro  Ser  Pro  Pro  Leu  Gly  Phe  Arg  Asp  Glu  His  Gly
     50                        55                        60

Val  Ala  Leu  Leu  Ala  Tyr  Thr  Ala  Asn  Ser  Pro  Leu  His  Lys  Glu  Phe
 65                       70                        75                        80

Asn  Ala  Ala  Val  Arg  Glu  Ala  Gly  Arg  Ser  Arg  Ala  His  Tyr  Leu  His
                    85                        90                        95

His  Phe  Ser  Phe  Lys  Thr  Leu  His  Phe  Leu  Leu  Thr  Glu  Ala  Leu  Gln
               100                       105                       110

Leu  Leu  Gly  Ser  Gly  Gln  Arg  Pro  Pro  Arg  Cys  His  Gln  Val  Phe  Arg
          115                       120                       125

Gly  Val  His  Gly  Leu  Arg  Phe  Arg  Pro  Ala  Gly  Pro  Arg  Ala  Thr  Val
     130                       135                       140

Arg  Leu  Gly  Gly  Phe  Ala  Ser  Ala  Ser  Leu  Lys  His  Val  Ala  Ala  Gln
145                      150                       155                       160

Gln  Phe  Gly  Glu  Asp  Thr  Phe  Phe  Gly  Ile  Trp  Thr  Cys  Leu  Gly  Ala
               165                       170                       175

Pro  Ile  Lys  Gly  Tyr  Ser  Phe  Phe  Pro  Gly  Glu  Glu  Glu  Val  Leu  Ile
               180                       185                       190

Pro  Pro  Phe  Glu  Thr  Phe  Gln  Val  Ile  Asn  Ala  Ser  Arg  Pro  Ala  Gln
          195                       200                       205

Gly  Pro  Ala  Arg  Ile  Tyr  Leu  Arg  Ala  Leu  Gly  Lys  His  Ser  Thr
     210                       215                       220
```

( 2 ) INFORMATION FOR SEQ ID NO:5:

( i ) SEQUENCE CHARACTERISTICS:
        ( A ) LENGTH: 18
        ( B ) TYPE: nucleic acid
        ( C ) STRANDEDNESS: double
        ( D ) TOPOLOGY: linear ( x i ) SEQUENCE DESCRIPTION: SEQ ID NO:5:

```
NTTRGAYATG  GCNCCNGC                                                                  18
```

( 2 ) INFORMATION FOR SEQ ID NO:6:

( i ) SEQUENCE CHARACTERISTICS:
        ( A ) LENGTH: 18
        ( B ) TYPE: nucleic acid
        ( C ) STRANDEDNESS: double
        ( D ) TOPOLOGY: linear ( x i ) SEQUENCE DESCRIPTION: SEQ ID NO:6:

NCTNGAYATG GCNCCNGC 18

( 2 ) INFORMATION FOR SEQ ID NO:7:

( i ) SEQUENCE CHARACTERISTICS:
        ( A ) LENGTH: 18
        ( B ) TYPE: nucleic acid
        ( C ) STRANDEDNESS: double
        ( D ) TOPOLOGY: linear ( x i ) SEQUENCE DESCRIPTION: SEQ ID NO:7:

YTTRCAYTGC ATYTCYTT 18

( 2 ) INFORMATION FOR SEQ ID NO:8:

( i ) SEQUENCE CHARACTERISTICS:
        ( A ) LENGTH: 18
        ( B ) TYPE: nucleic acid
        ( C ) STRANDEDNESS: double
        ( D ) TOPOLOGY: linear ( x i ) SEQUENCE DESCRIPTION: SEQ ID NO:8:

NTTYGAYGAY CARTAYGT 18

( 2 ) INFORMATION FOR SEQ ID NO:9:

( i ) SEQUENCE CHARACTERISTICS:
        ( A ) LENGTH: 18
        ( B ) TYPE: nucleic acid
        ( C ) STRANDEDNESS: double
        ( D ) TOPOLOGY: linear ( x i ) SEQUENCE DESCRIPTION: SEQ ID NO:9:

DATRTAYTCR CARTTRTA 18

( 2 ) INFORMATION FOR SEQ ID NO:10:

( i ) SEQUENCE CHARACTERISTICS:
        ( A ) LENGTH: 25
        ( B ) TYPE: nucleic acid
        ( C ) STRANDEDNESS: double
        ( D ) TOPOLOGY: linear ( x i ) SEQUENCE DESCRIPTION: SEQ ID NO:10:

GCTGTCTGCA TACACCTGGT TTGGC 25

( 2 ) INFORMATION FOR SEQ ID NO:11:

( i ) SEQUENCE CHARACTERISTICS:
        ( A ) LENGTH: 21
        ( B ) TYPE: nucleic acid
        ( C ) STRANDEDNESS: double
        ( D ) TOPOLOGY: linear ( x i ) SEQUENCE DESCRIPTION: SEQ ID NO:11:

GTCGTTGAGA TCCGGGAGAG C 21

( 2 ) INFORMATION FOR SEQ ID NO:12:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO:12:

CCCGCATCTA CCTCCGAGCC                                                                                 20

( 2 ) INFORMATION FOR SEQ ID NO:13:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO:13:

CAAGCACAGC ACCTATAATT                                                                                 20

( 2 ) INFORMATION FOR SEQ ID NO:14:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO:14:

GCCCANCCAT CNGCATANAC                                                                                 20

( 2 ) INFORMATION FOR SEQ ID NO:15:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO:15:

GCTAANGCCC ANCCATCNGC                                                                                 20

( 2 ) INFORMATION FOR SEQ ID NO:16:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO:16:

GCNAGNGCCC ANCCATCNGC                                                                                 20

( 2 ) INFORMATION FOR SEQ ID NO:17:

( i ) SEQUENCE CHARACTERISTICS:
        ( A ) LENGTH: 25
        ( B ) TYPE: nucleic acid
        ( C ) STRANDEDNESS: double
        ( D ) TOPOLOGY: linear ( x i ) SEQUENCE DESCRIPTION: SEQ ID NO:17:

CAAAAGCTGG AGCTCCACCG CGGTG                                                                           25

( 2 ) INFORMATION FOR SEQ ID NO:18:

( i ) SEQUENCE CHARACTERISTICS:
   ( A ) LENGTH: 21
   ( B ) TYPE: nucleic acid
   ( C ) STRANDEDNESS: double
   ( D ) TOPOLOGY: linear ( x i ) SEQUENCE DESCRIPTION: SEQ ID NO:18:

GCTCTAGAAC TAGTGGATCC C 21

( 2 ) INFORMATION FOR SEQ ID NO:19:

( i ) SEQUENCE CHARACTERISTICS:
      ( A ) LENGTH: 20
      ( B ) TYPE: nucleic acid
      ( C ) STRANDEDNESS: double
      ( D ) TOPOLOGY: linear ( x i ) SEQUENCE DESCRIPTION: SEQ ID NO:19:

TGTCATGGCT GCTGCACAGC 20

( 2 ) INFORMATION FOR SEQ ID NO:20:

( i ) SEQUENCE CHARACTERISTICS:
      ( A ) LENGTH: 32
      ( B ) TYPE: nucleic acid
      ( C ) STRANDEDNESS: double
      ( D ) TOPOLOGY: linear ( x i ) SEQUENCE DESCRIPTION: SEQ ID NO:20:

CAUCAUCAUC AUACGTACTG GTCATCAAAG GA 32

( 2 ) INFORMATION FOR SEQ ID NO:21:

( i ) SEQUENCE CHARACTERISTICS:
      ( A ) LENGTH: 57
      ( B ) TYPE: nucleic acid
      ( C ) STRANDEDNESS: double
      ( D ) TOPOLOGY: linear ( x i ) SEQUENCE DESCRIPTION: SEQ ID NO:21:

AAGGATCCGT CGACATCGAT AATACGACTC ACTATAGGGA TTTTTTTTTT TTTTTTT 57

( 2 ) INFORMATION FOR SEQ ID NO:22:

( i ) SEQUENCE CHARACTERISTICS:
      ( A ) LENGTH: 17
      ( B ) TYPE: nucleic acid
      ( C ) STRANDEDNESS: double
      ( D ) TOPOLOGY: linear ( x i ) SEQUENCE DESCRIPTION: SEQ ID NO:22:

AAGGATCCGT CGACATC 17

( 2 ) INFORMATION FOR SEQ ID NO:23:

( i ) SEQUENCE CHARACTERISTICS:
      ( A ) LENGTH: 37
      ( B ) TYPE: nucleic acid
      ( C ) STRANDEDNESS: double
      ( D ) TOPOLOGY: linear ( x i ) SEQUENCE DESCRIPTION: SEQ ID NO:23:

CUACUACUAC UAGACATCGA TAATACGACT CACTATA 37

( 2 ) INFORMATION FOR SEQ ID NO:24:

( i ) SEQUENCE CHARACTERISTICS:
      ( A ) LENGTH: 39

(B) TYPE: nucleic acid
(C) STRANDEDNESS: double
(D) TOPOLOGY: linear (xi) SEQUENCE DESCRIPTION: SEQ ID NO:24:

CTGGTTCCGG CGACATATGA GCCACCTGGT CACACGTCG                    39

(2) INFORMATION FOR SEQ ID NO:25:

(i) SEQUENCE CHARACTERISTICS:
(A) LENGTH: 42
(B) TYPE: nucleic acid
(C) STRANDEDNESS: double
(D) TOPOLOGY: linear (xi) SEQUENCE DESCRIPTION: SEQ ID NO:25:

CTCGCTCCGG CGAGGATCCT CAGGAGAGGC GCTCCTGAGC CG                42

(2) INFORMATION FOR SEQ ID NO:26:

(i) SEQUENCE CHARACTERISTICS:
(A) LENGTH: 48
(B) TYPE: nucleic acid
(C) STRANDEDNESS: double
(D) TOPOLOGY: linear (xi) SEQUENCE DESCRIPTION: SEQ ID NO:26:

TTACTTTCCT CATCTAGGCC TTGTCCGGGG CAGGGGAGCT GGTGTTGG          48

(2) INFORMATION FOR SEQ ID NO:27:

(i) SEQUENCE CHARACTERISTICS:
(A) LENGTH: 48
(B) TYPE: nucleic acid
(C) STRANDEDNESS: double
(D) TOPOLOGY: linear (xi) SEQUENCE DESCRIPTION: SEQ ID NO:27:

AAAGGAGGCC GGGGCCATGT CCAGCGGTGT CTCTTGAGAG AAGAGGTC          48

(2) INFORMATION FOR SEQ ID NO:28:

(i) SEQUENCE CHARACTERISTICS:
(A) LENGTH: 48
(B) TYPE: nucleic acid
(C) STRANDEDNESS: double
(D) TOPOLOGY: linear (xi) SEQUENCE DESCRIPTION: SEQ ID NO:28:

AGGAATGTCC AGAGTCTGGG GGGTCAGAAG AGGCCTGGGC TTCCTGGG          48

(2) INFORMATION FOR SEQ ID NO:29:

(i) SEQUENCE CHARACTERISTICS:
(A) LENGTH: 24
(B) TYPE: nucleic acid
(C) STRANDEDNESS: double
(D) TOPOLOGY: linear (xi) SEQUENCE DESCRIPTION: SEQ ID NO:29:

CGGTTGGTCC ACATACGTCT GTCG                                    24

(2) INFORMATION FOR SEQ ID NO:30:

(i) SEQUENCE CHARACTERISTICS:
(A) LENGTH: 33
(B) TYPE: nucleic acid
(C) STRANDEDNESS: double (D) TOPOLOGY: linear (xi) SEQUENCE DESCRIPTION: SEQ ID NO:30:

CAUCAUCAUC AUGTGGTTGA GATCCGGGAG AGC 33

(2) INFORMATION FOR SEQ ID NO:31:

(i) SEQUENCE CHARACTERISTICS:
        (A) LENGTH: 30
        (B) TYPE: nucleic acid
        (C) STRANDEDNESS: double
        (D) TOPOLOGY: linear (xi) SEQUENCE DESCRIPTION: SEQ ID NO:31:

ACTAGTTATG CAACCGACAC GACGACGGTA 30

(2) INFORMATION FOR SEQ ID NO:32:

(i) SEQUENCE CHARACTERISTICS:
        (A) LENGTH: 20
        (B) TYPE: nucleic acid
        (C) STRANDEDNESS: double
        (D) TOPOLOGY: linear (xi) SEQUENCE DESCRIPTION: SEQ ID NO:32:

CCCGCATCTA CCTCCGAGCC 20

(2) INFORMATION FOR SEQ ID NO:33:

(i) SEQUENCE CHARACTERISTICS:
        (A) LENGTH: 32
        (B) TYPE: nucleic acid
        (C) STRANDEDNESS: double
        (D) TOPOLOGY: linear (xi) SEQUENCE DESCRIPTION: SEQ ID NO:33:

CAUCAUCAU CAUCAAGCAC AGCACCTATAA TT 32

(2) INFORMATION FOR SEQ ID NO:34:

(i) SEQUENCE CHARACTERISTICS:
        (A) LENGTH: 24
        (B) TYPE: nucleic acid
        (C) STRANDEDNESS: double
        (D) TOPOLOGY: linear (xi) SEQUENCE DESCRIPTION: SEQ ID NO:34:

GGACTCCTAC AACGGGTACA CACG 24

(2) INFORMATION FOR SEQ ID NO:35:

(i) SEQUENCE CHARACTERISTICS:
        (A) LENGTH: 36
        (B) TYPE: nucleic acid
        (C) STRANDEDNESS: double
        (D) TOPOLOGY: linear (xi) SEQUENCE DESCRIPTION: SEQ ID NO:35:

CUACUACUAC UAAGCAACT GGCCCAGGGTC ACCAGC 36

(2) INFORMATION FOR SEQ ID NO:36:

(i) SEQUENCE CHARACTERISTICS:
        (A) LENGTH: 30
        (B) TYPE: nucleic acid
        (C) STRANDEDNESS: double
        (D) TOPOLOGY: linear ( x i ) SEQUENCE DESCRIPTION: SEQ ID NO:36:

```
ACGTACTCTG TGCCCTGTCA UCAUCAUCAU                                                    30
```

( 2 ) INFORMATION FOR SEQ ID NO:37:

( i ) SEQUENCE CHARACTERISTICS:
        ( A ) LENGTH: 1305 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 73..1047

( x i ) SEQUENCE DESCRIPTION: SEQ ID NO:37:

```
TTCCACCAGG ACAGGCCTAG ATGAGGAAAC TGAGACCCAA AAAGAGACAG CAACTGGCCC                    60

AGGGTCACCA GC ATG CAG ATG CCT GCT ATG ATG TCT CTG CTT CTT GTG                      108
              Met Gln Met Pro Ala Met Met Ser Leu Leu Leu Val
               1               5                          10

TCT GTG GGC CTC ATG GAA GCA CTT CAG GCC CAG AGC CAC CCC ATC ACA                     156
Ser Val Gly Leu Met Glu Ala Leu Gln Ala Gln Ser His Pro Ile Thr
         15                  20                  25

CGA CGA GAC CTC TTC TCT CAA GAG ATT CAG CTG GAC ATG GCC CTG GCC                     204
Arg Arg Asp Leu Phe Ser Gln Glu Ile Gln Leu Asp Met Ala Leu Ala
     30                  35                  40

TCC TTT GAT GAC CAG TAC GCT GGC TGT GCT GCT GCC ATG ACA GCT GCT                     252
Ser Phe Asp Asp Gln Tyr Ala Gly Cys Ala Ala Ala Met Thr Ala Ala
 45                  50                  55                  60

CTC CCG GAT CTC AAC CAC ACG GAG TTC CAG GCC AAC CAG GTG TAT GCA                     300
Leu Pro Asp Leu Asn His Thr Glu Phe Gln Ala Asn Gln Val Tyr Ala
                 65                  70                  75

GAC AGC TGG ACA CTG GCA AGC AGC CAA TGG CAG GAG CGT CAG GCC AGG                     348
Asp Ser Trp Thr Leu Ala Ser Ser Gln Trp Gln Glu Arg Gln Ala Arg
             80                  85                  90

TGG CCA GAG TGG AGT CTC AGC CCC ACC CGT CCA TCC CCG CCA CCC CTG                     396
Trp Pro Glu Trp Ser Leu Ser Pro Thr Arg Pro Ser Pro Pro Pro Leu
         95                 100                 105

GGC TTC CGC GAT GAG CAT GGG GTG GCC CTC CTG GCC TAC ACA GCC AAC                     444
Gly Phe Arg Asp Glu His Gly Val Ala Leu Leu Ala Tyr Thr Ala Asn
     110                 115                 120

AGC CCC CTG CAC AAG GAG TTC AAT GCA GCC GTG CGT GAG GCG GGC CGC                     492
Ser Pro Leu His Lys Glu Phe Asn Ala Ala Val Arg Glu Ala Gly Arg
125                 130                 135                 140

TCC CGG GCC CAC TAC CTC CAC CAC TTC TCC TTC AAG ACA CTC CAT TTC                     540
Ser Arg Ala His Tyr Leu His His Phe Ser Phe Lys Thr Leu His Phe
                 145                 150                 155

CTG CTG ACT GAG GCC CTG CAG CTC CTG GGC AGC GGC CAG CGT CCA CCC                     588
Leu Leu Thr Glu Ala Leu Gln Leu Leu Gly Ser Gly Gln Arg Pro Pro
             160                 165                 170

CGG TGC CAC CAG GTG TTC CGA GGT GTG CAC GGC CTG CGC TTC CGG CCA                     636
Arg Cys His Gln Val Phe Arg Gly Val His Gly Leu Arg Phe Arg Pro
         175                 180                 185

GCA GGG CCC CGG GCC ACC GTG AGG CTG GGG GGC TTT GCT TCT GCC TCC                     684
Ala Gly Pro Arg Ala Thr Val Arg Leu Gly Gly Phe Ala Ser Ala Ser
     190                 195                 200

CTG AAG CAT GTT GCA GCC CAG CAG TTT GGT GAG GAC ACC TTC TTC GGC                     732
```

| | | | | | | | | | | | | | | | | |
|---|---|---|---|---|---|---|---|---|---|---|---|---|---|---|---|---|
|Leu|Lys|His|Val|Ala|Ala|Gln|Gln|Phe|Gly|Glu|Asp|Thr|Phe|Phe|Gly| |
|205| | | |210| | | |215| | | |220| | | | |

| | | | | | | | | | | | | | | | | |
|---|---|---|---|---|---|---|---|---|---|---|---|---|---|---|---|---|
|ATC|TGG|ACC|TGC|CTT|GGG|GCC|CCT|ATC|AAG|GGC|TAC|TCC|TTC|TTC|CCT|780|
|Ile|Trp|Thr|Cys|Leu|Gly|Ala|Pro|Ile|Lys|Gly|Tyr|Ser|Phe|Phe|Pro| |
| | | |225| | | |230| | | |235| | | | | |

| | | | | | | | | | | | | | | | | |
|---|---|---|---|---|---|---|---|---|---|---|---|---|---|---|---|---|
|GGA|GAG|GAA|GAG|GTG|CTG|ATC|CCC|CCC|TTT|GAG|ACC|TTC|CAA|GTG|ATC|828|
|Gly|Glu|Glu|Glu|Val|Leu|Ile|Pro|Pro|Phe|Glu|Thr|Phe|Gln|Val|Ile| |
| | | |240| | | |245| | | |250| | | | | |

| | | | | | | | | | | | | | | | | |
|---|---|---|---|---|---|---|---|---|---|---|---|---|---|---|---|---|
|AAT|GCC|AGC|AGA|CCG|GCC|CAG|GGC|CCC|GCC|CGC|ATC|TAC|CTC|CGA|GCC|876|
|Asn|Ala|Ser|Arg|Pro|Ala|Gln|Gly|Pro|Ala|Arg|Ile|Tyr|Leu|Arg|Ala| |
| | |255| | | |260| | | |265| | | | | | |

| | | | | | | | | | | | | | | | | |
|---|---|---|---|---|---|---|---|---|---|---|---|---|---|---|---|---|
|CTG|GGC|AAG|CAC|AGC|ACC|TAC|AAC|TGC|GAG|TAC|ATC|AAA|GAC|AAG|AAG|924|
|Leu|Gly|Lys|His|Ser|Thr|Tyr|Asn|Cys|Glu|Tyr|Ile|Lys|Asp|Lys|Lys| |
| |270| | | |275| | | |280| | | | | | | |

| | | | | | | | | | | | | | | | | |
|---|---|---|---|---|---|---|---|---|---|---|---|---|---|---|---|---|
|TGC|AAG|TCT|GGG|CCT|TGC|CAT|CTG|GAT|AAT|TCA|GCC|ATG|GGT|CAG|AGC|972|
|Cys|Lys|Ser|Gly|Pro|Cys|His|Leu|Asp|Asn|Ser|Ala|Met|Gly|Gln|Ser| |
|285| | | |290| | | |295| | | |300| | | | |

| | | | | | | | | | | | | | | | | |
|---|---|---|---|---|---|---|---|---|---|---|---|---|---|---|---|---|
|CCC|CTC|TCT|GCA|GTC|TGG|TCT|TTG|CTG|CTG|CTG|CTC|TGG|TTC|CTC|GTG|1020|
|Pro|Leu|Ser|Ala|Val|Trp|Ser|Leu|Leu|Leu|Leu|Leu|Trp|Phe|Leu|Val| |
| | | |305| | | |310| | | |315| | | | | |

| | | | | | | | | | | | | |
|---|---|---|---|---|---|---|---|---|---|---|---|---|
|GTG|AGG|GCC|TTT|CCA|GAT|GGT|CCA|GGC|CTC|CTT|TGATGCATGA GACA|1067|
|Val|Arg|Ala|Phe|Pro|Asp|Gly|Pro|Gly|Leu|Leu| | |
| | |320| | | |325| | | | | | |

| | | | | | |
|---|---|---|---|---|---|
|CGGGAC|AGCCTCGCCTGCTG|CCTCTGCCCA|TCCTGAGGAT|GTTGGCCATG|TGTGCTTCAG|1127|
|TGTAACCAAG|ATTCCTGTCA|ATCCCATCTG|CAGGGAACTC|TGGGACCTTC|TCTGGTAGCT|1187|
|GCCAGACCGG|CTGGTGGAGA|AACAGGAGAC|AATCTGGGGA|CTGAACCTTA|CCCAGGGCTG|1247|
|TAGGAGTGAG|ACTCTGAATA|AAGGGTTGGG|CCGGCAAAAA|AAAAAAAAA|AAAAAAA|1305|

( 2 ) INFORMATION FOR SEQ ID NO:38:

( i ) SEQUENCE CHARACTERISTICS:
        ( A ) LENGTH: 327 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

| | | | | | | | | | | | | | | | |
|---|---|---|---|---|---|---|---|---|---|---|---|---|---|---|---|
|Met|Gln|Met|Pro|Ala|Met|Met|Ser|Leu|Leu|Leu|Val|Ser|Val|Gly|Leu|
|1| | | |5| | | |10| | | |15| | | |

| | | | | | | | | | | | | | | | |
|---|---|---|---|---|---|---|---|---|---|---|---|---|---|---|---|
|Met|Glu|Ala|Leu|Gln|Ala|Gln|Ser|His|Pro|Ile|Thr|Arg|Arg|Asp|Leu|
| | | |20| | | |25| | | |30| | | | |

| | | | | | | | | | | | | | | | |
|---|---|---|---|---|---|---|---|---|---|---|---|---|---|---|---|
|Phe|Ser|Gln|Glu|Ile|Gln|Leu|Asp|Met|Ala|Leu|Ala|Ser|Phe|Asp|Asp|
| | |35| | | |40| | | |45| | | | | |

| | | | | | | | | | | | | | | | |
|---|---|---|---|---|---|---|---|---|---|---|---|---|---|---|---|
|Gln|Tyr|Ala|Gly|Cys|Ala|Ala|Ala|Met|Thr|Ala|Ala|Leu|Pro|Asp|Leu|
| |50| | | |55| | | |60| | | | | | |

| | | | | | | | | | | | | | | | |
|---|---|---|---|---|---|---|---|---|---|---|---|---|---|---|---|
|Asn|His|Thr|Glu|Phe|Gln|Ala|Asn|Gln|Val|Tyr|Ala|Asp|Ser|Trp|Thr|
|65| | | |70| | | |75| | | |80| | | |

| | | | | | | | | | | | | | | | |
|---|---|---|---|---|---|---|---|---|---|---|---|---|---|---|---|
|Leu|Ala|Ser|Ser|Gln|Trp|Gln|Glu|Arg|Gln|Ala|Arg|Trp|Pro|Glu|Trp|
| | | |85| | | |90| | | |95| | | | |

| | | | | | | | | | | | | | | | |
|---|---|---|---|---|---|---|---|---|---|---|---|---|---|---|---|
|Ser|Leu|Ser|Pro|Thr|Arg|Pro|Ser|Pro|Pro|Leu|Gly|Phe|Arg|Asp|
| | |100| | | |105| | | |110| | | | | |

| | | | | | | | | | | | | | | | |
|---|---|---|---|---|---|---|---|---|---|---|---|---|---|---|---|
|Glu|His|Gly|Val|Ala|Leu|Leu|Ala|Tyr|Thr|Ala|Asn|Ser|Pro|Leu|His|
| | |115| | | |120| | | |125| | | | | |

| | | | | | | | | | | | | | | | |
|---|---|---|---|---|---|---|---|---|---|---|---|---|---|---|---|
|Lys|Glu|Phe|Asn|Ala|Ala|Val|Arg|Glu|Ala|Gly|Arg|Ser|Arg|Ala|His|
| |130| | | |135| | | |140| | | | | | |

| | | | | | | | | | | | | | | | |
|---|---|---|---|---|---|---|---|---|---|---|---|---|---|---|---|
|Tyr|Leu|His|His|Phe|Ser|Phe|Lys|Thr|Leu|His|Phe|Leu|Leu|Thr|Glu|
|145| | | |150| | | |155| | | |160| | | |

| | | | | | | | | | | | | | | |
|---|---|---|---|---|---|---|---|---|---|---|---|---|---|---|
| Ala | Leu | Gln | Leu | Leu<br>165 | Gly | Ser | Gly | Gln | Arg<br>170 | Pro | Pro | Arg | Cys | His<br>175 | Gln |
| Val | Phe | Arg | Gly<br>180 | Val | His | Gly | Leu | Arg<br>185 | Phe | Arg | Pro | Ala | Gly<br>190 | Pro | Arg |
| Ala | Thr | Val<br>195 | Arg | Leu | Gly | Gly | Phe<br>200 | Ala | Ser | Ala | Ser | Leu<br>205 | Lys | His | Val |
| Ala | Ala<br>210 | Gln | Gln | Phe | Gly | Glu<br>215 | Asp | Thr | Phe | Phe | Gly<br>220 | Ile | Trp | Thr | Cys |
| Leu<br>225 | Gly | Ala | Pro | Ile | Lys<br>230 | Gly | Tyr | Ser | Phe | Phe<br>235 | Pro | Gly | Glu | Glu | Glu<br>240 |
| Val | Leu | Ile | Pro | Pro<br>245 | Phe | Glu | Thr | Phe | Gln<br>250 | Val | Ile | Asn | Ala | Ser<br>255 | Arg |
| Pro | Ala | Gln | Gly<br>260 | Pro | Ala | Arg | Ile | Tyr<br>265 | Leu | Arg | Ala | Leu | Gly<br>270 | Lys | His |
| Ser | Thr | Tyr<br>275 | Asn | Cys | Glu | Tyr | Ile<br>280 | Lys | Asp | Lys | Lys | Cys<br>285 | Lys | Ser | Gly |
| Pro | Cys<br>290 | His | Leu | Asp | Asn | Ser<br>295 | Ala | Met | Gly | Gln | Ser<br>300 | Pro | Leu | Ser | Ala |
| Val<br>305 | Trp | Ser | Leu | Leu | Leu<br>310 | Leu | Leu | Trp | Phe | Leu<br>315 | Val | Val | Arg | Ala | Phe<br>320 |
| Pro | Asp | Gly | Pro | Gly<br>325 | Leu | Leu | | | | | | | | | |

What is claimed is:

1. An isolated or purified gene sequence encoding rabbit skeletal muscle ADP-ribosyltransferase having the sequence shown in SEQ ID NO: 1.

2. An isolated or purified gene sequence encoding human ADP-ribosyltransferase having the sequence shown in SEQ ID NO: 3.

3. A recombinant vector comprising the gene sequence of claim 1.

4. A recombinant vector comprising the gene sequence of claim 2.

5. A host cell comprising the recombinant vector of claim 3.

6. A host cell comprising the recombinant vector of claim 4.

* * * * *